United States Patent [19]

Jones et al.

[11] 4,082,735

[45] Apr. 4, 1978

[54] NOVEL IMMUNOLOGICAL ADJUVANT COMPOUNDS AND METHODS OF PREPARATION THEREOF

[75] Inventors: Gordon H. Jones, Cupertino; John G. Moffatt, Los Altos; John J. Nestor, Jr., Sunnyvale, all of Calif.

[73] Assignee: Syntex (U.S.A.) Inc., Palo Alto, Calif.

[21] Appl. No.: 680,260

[22] Filed: Apr. 26, 1976

[51] Int. Cl.$^2$ ................. C07C 103/52; A61K 37/00
[52] U.S. Cl. ........................... 260/112.5 R; 424/177
[58] Field of Search ................. 260/112.5 R; 424/177

[56] References Cited

U.S. PATENT DOCUMENTS 3,960,828  6/1976  Meienhofer ................... 260/112.5 R

OTHER PUBLICATIONS

Biochemical and Biophysical Research Communication, 59, (1974) pp. 1317–1325.

*Primary Examiner*—Delbert R. Phillips

*Attorney, Agent, or Firm*—Gerard A. Blaufarb

[57] ABSTRACT

This application relates to novel immunological adjuvant compounds of the formula:

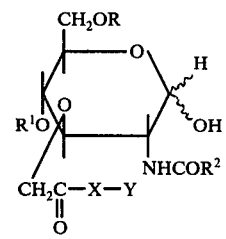

wherein each of R and R$^1$ are the same or different and are hydrogen or an acyl radical; R$^2$ is an unsubstituted or substituted alkyl radical, or an unsubstituted or substituted aryl radical; X is an aminoacyl moiety; and Y is D-isoasparagine or D-isoglutamine.

50 Claims, No Drawings

NOVEL IMMUNOLOGICAL ADJUVANT COMPOUNDS AND METHODS OF PREPARATION THEREOF

This invention relates to novel immunological adjuvant compounds of the formula:

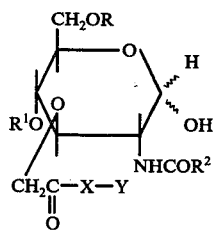

wherein each of R and $R^1$ are the same or different and are selected from the group consisting of hydrogen or an acyl radical containing from 1 to 22 carbon atoms;

$R^2$ is selected from the group consisting of an unsubstituted or substituted alkyl radical containing from 1 to 21 carbon atoms, or an unsubstituted or substituted aryl radical containing from 6 to 10 carbon atoms;

X is an aminoacyl moiety selected from the group consisting of
L-alanyl,
L-valyl,
L-leucyl,
L-isoleucyl,
L-α-aminobutyryl,
L-seryl,
L-threonyl,
L-methionyl,
L-cysteinyl,
L-phenylalanyl,
L-tyrosyl,
L-tryptophanyl,
L-lysyl,
L-ornithyl,
L-arginyl,
L-histidyl,
L-glutamyl,
L-glutaminyl
L-aspartyl,
L-asparaginyl,
L-prolyl, or
L-hydroxyprolyl;

Y is an aminoacyl moiety selected from the group consisting of D-isoasparagine or D-isoglutamine; and the wavy line (ξ) represents the α- or β- configuration or mixtures thereof, with the proviso that when one wavy line is α, the other is β.

Particularly preferred are those compounds of Formula (I) wherein X is selected from the group consisting of L-alanyl, L-valyl, L-seryl or L-prolyl and Y is D-isoglutamine.

In the field of immunology, more than one injection of a vaccine (or bacterin) is usually required to achieve the immunological response in a host sufficient to ward off a viral (or bacterial) infection. This is because the viral (or bacterial) antigen contained in the vaccine (or bacterin) is cleared from the site of injection by the animal (or human) host too rapidly and the host has an insufficient length of time to build up its immune response.

In order to delay the release of the viral (or bacterial) antigen, and to generally stimulate the host's immunological systems, immunological adjuvants have been added to vaccines (or bacterins) in an effort to avoid the necessity of multiple injections. However, many of these earlier immunological adjuvants, e.g., kaolin, gum tragacanth, bentonite, carbopols, calcium phosphate gels, tapioca, alum, aluminum hydroxide, calcium chloride, sodium alginate, and the like, have the drawback of being unmetabolizeable when injected and thus these immunological adjuvants themselves became a source of irritation.

The art has long sought an immunological adjuvant material which would be readily metabolizeable by the host and, at the same time, delay the release of the antigen and generally stimulate its immune response.

Commonly used laboratory immunological adjuvants are (a) Freund's Complete Adjuvant (FCA) which is a suspension of killed whole Mycobacterium tuberculosis in mineral oil plus an emulsifier; and (b) Freund's Incomplete Adjuvant (FIA) which is mineral oil plus an emulsifier only. Notwithstanding that FCA and FIA are used as laboratory standards they are not used commercially because FCA is derived from the virulent microorganism, Mycobacterium tuberculosis; and FIA, absent the presence of the killed Mycobacterium tuberculosis, does not produce a high enough immunological response.

Ellouz et al., Biochemical and Biophysical Research Communications, Vol. 59, No. 4, pages 1317–1325 (1974), (see also Belgian Pat. No. 821,385), disclose that certain peptidoglycans obtained from microorganisms possess immunological adjuvant activity and can be used in place of the whole killed Mycobacterium tuberculosis in FCA.

The novel peptidoglycans of Formula (I) possess significant immunological adjuvant activity, e.g., as measured by antibody titres to either bovine serum albumin (BSA) or ovalbumin [see W. J. Herbert, Ch. 20, Vol. 1, Handbook of Experimental Immunology, Editor D. M. Weir, Blackwell Scientific Publications, Oxford (1973)], and delayed hypersensitivity to either BSA or ovalbumin [see J. H. Humphrey and R. G. White, Immunology for Students of Medicine, pages 493–545; Publisher F. A. Davis Co., Philadelphia, 3rd Edition (1970)] or delayed hypersensitivity to arsanilic tyrosine [see S. Laskowitz, J. Exp. Med., 119, 291 (1963) and S. Laskowitz, Science, 155,350 (1976)], as described more fully in Example 16; and possess fewer deleterious side effects as described more fully in Example 17. In addition, it has also surprisingly been found that the compounds of Formula (I), when incorporated into a vaccine (or bacterin) composition also containing a mineral oil or vegetable oil, do not show the adverse side effects ordinarily observed when mineral and vegetable oils are used in vaccine (or bacterin) compositions containing FCA.

Furthermore, the compounds of Formula (I) have per se activity against infectious organism, e.g., *Klebsiella pneumoniae, Escherichia coli, Candida albicans,* or *Staphylococcus aureus.*

The novel compounds of Formula (I) can be prepared according to the following reaction scheme:

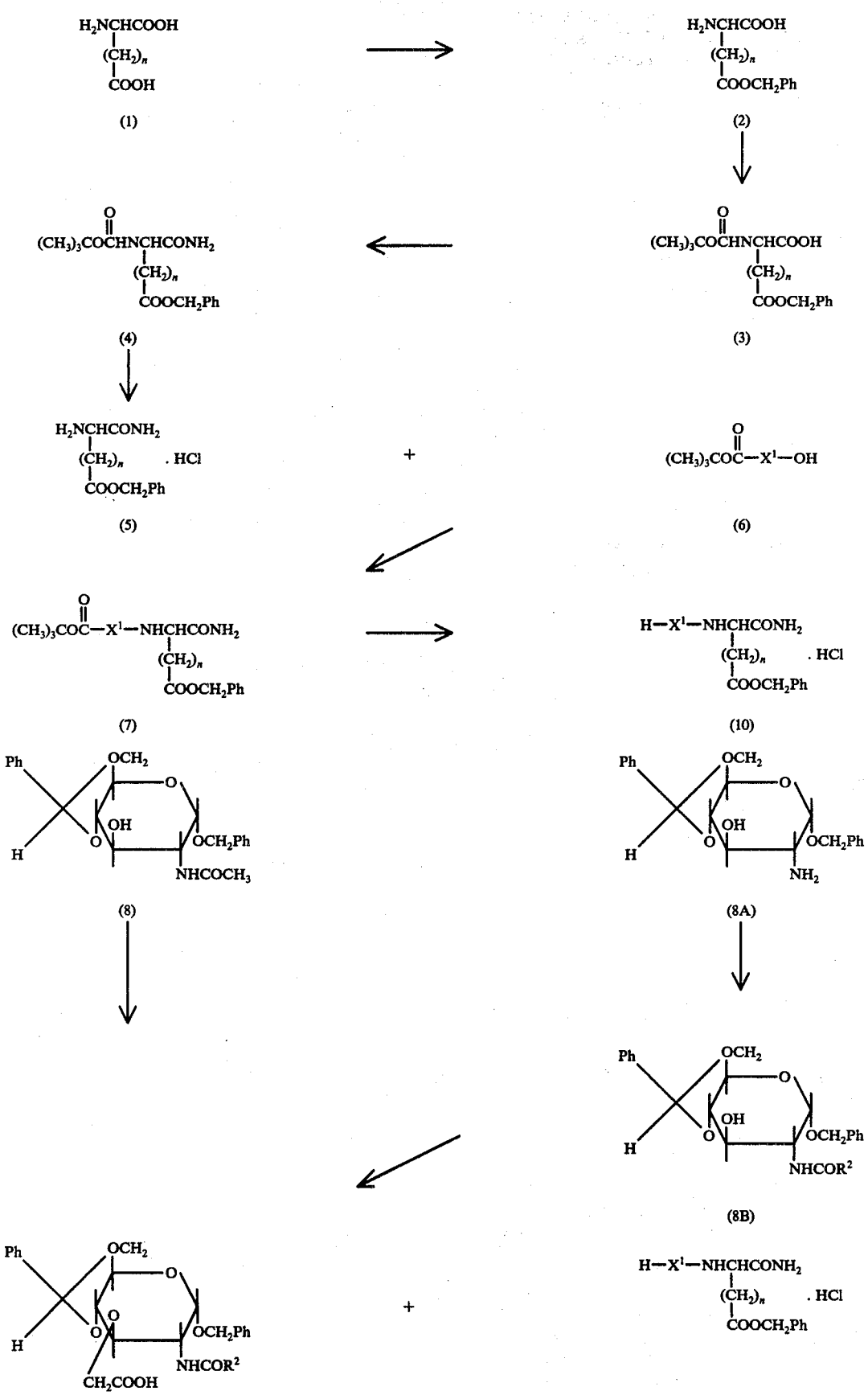

-continued
(9)
(10)
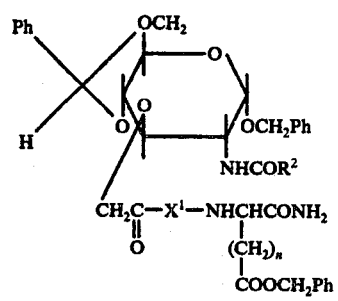
(11)
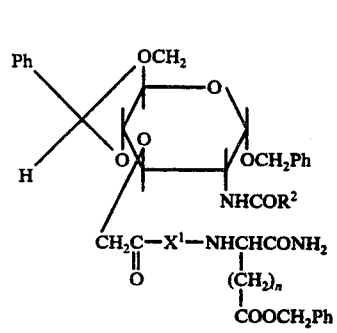
(11)
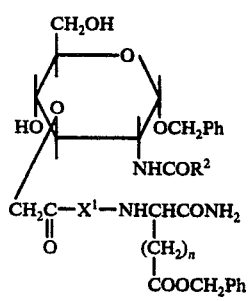
(12A)
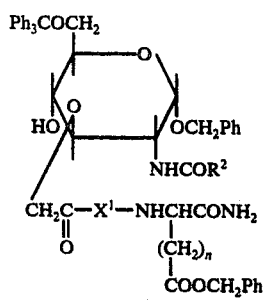
(13)
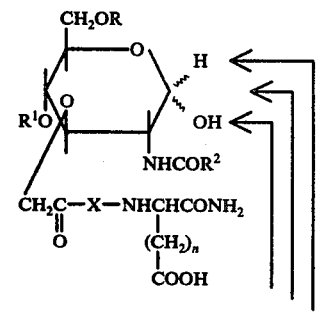
(12E)
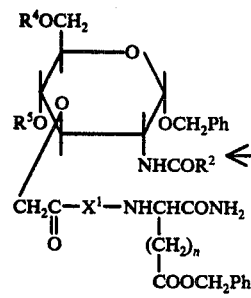
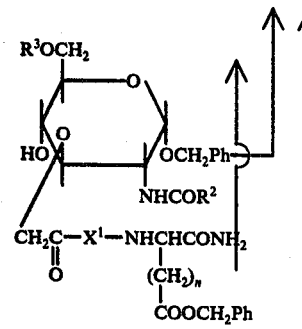

(12B)

↓

[Structure 12C: Ph₃COCH₂ group, pyranose ring with R³O, OCH₂Ph, NHCOR², and CH₂C—X¹—NHCHCONH₂ with (CH₂)ₙ and COOCH₂Ph substituents]

(12C)

→

(12F)

↑

[Structure 12D: CH₂OH group, pyranose ring with R³O, OCH₂Ph, NHCOR², and CH₂C—X¹—NHCHCONH₂ with (CH₂)ₙ and COOCH₂Ph substituents]

(12D)

wherein

R, R¹, R², X and the wavy line (ξ) are defined as above;
R³ is an acyl radical containing from 1 to 22 carbon atoms;
R⁴ and R⁵ are the same or different acyl radical containing from 1 to 22 carbon atoms;
n is the whole integer 1 to 2;
Ph is phenyl; and
X¹ is selected from the group consisting of
L-alanyl,
L-valyl,
L-leucyl,
L-isoleucyl,
L-α-aminobutyryl,
O-benzyl-L-seryl,
O-benzyl-L-threonyl,
L-methionyl,
S-benzyl-L-cysteinyl,
L-phenylalanyl,
O-benzyl-L-tyrosyl,
L-tryptophanyl,
ε-carbobenzyloxy-L-lysyl,
δ-carbobenzyloxy-L-ornithyl,
gu-nitro-L-arginyl,
N$^{Im}$-benzyl-L-histidyl,
γ-benzyl ester of L-glutamyl,
L-glutaminyl,
β-benzyl ester of L-aspartyl,
L-asparaginyl,
L-prolyl, or
O-benzyl-L-hydroxyprolyl, It will be observed that in the compound of Formula (13) when n is the integer 1 or 2, the compounds thus obtained are the compounds of Formula (I) in which Y is D-isoasparagine or D-isoglutamine, respectively.

In practicing the above process a D-amino acid of Formula (I) is treated with an aralkyl alcohol such as benzyl alcohol, p-methoxybenzyl alcohol, p-nitrobenzyl alcohol and the like, preferably benzyl alcohol, in the presence of a strong acid such as hydrogen chloride, p-toluenesulfonic acid, and the like, preferably sulfuric acid, at a temperature of from about 0° to about 40° C, preferably 20°–25° C, for from about 8 to about 40 hours, preferably 14–18 hours, to obtain a compound of Formula (2).

The amino grouping of the thus-obtained amino ester of Formula (2) is protected by blocking with a selectively removable group such as those well known to the art of polypeptide synthesis and generally denominated as acyl (e.g., formyl, triflurooacetyl, phthalyl, and the like); urethane (e.g., t-butyloxycarbonyl, p-methoxybenzyloxycarbonyl, 2-(p-biphenyl)isopropyloxycarbonyl, isonicotinyloxycarbonyl, and the like); sulfenyl (o-nitrophenylsulfenyl, tritylsulfenyl, and the like); or alkyl (triphenylmethyl, benzyhydryl, and the like). More particularly, the protected amino ester of Formula (3), the N$^{60}$-t-butyloxycarbonyl derivative, is prepared by reacting the amino ester of Formula (2) with a suitable reagent (e.g., t-butylfluoroformate,t-butylazidoformate, t-butylphenyl carbonate or the like, preferably t-butylazidoformate) in an aqueous-organic mixture or in an anhydrous organic solvent (e.g., dioxane, tetrahydrofuran, dimethylformamide, dimethylsulfoxide, and the like, preferably anhydrous dimethylsulfoxide) in the presence of a base (e.g., sodium hydroxide, magnesium oxide, tetramethylguanidine, triethylamine and the like, pregerably triethylamine), for from about 12 to about 48 hours, preferably 20–24 hours, at from about 0° to about 40° C, preferably 20°–25° C.

The carboxyl grouping of a protected amino ester of Formula (3) is activated by one of the reagents customarily used for amide bond formation (e.g., N,N'-dicyclohexylcarbodiimide, N,N'-diisopropylcarbodiimide, or other carbodiimide, either with or without an additive such as N-hydroxysuccinimide or 1-hydroxybenzotriazole; isobutylchloroformate or other chloroformate; 2-ethyl-5-(3-sulfophenyl)-1,2-oxazole-betaine or other 1,2-oxazolium salt; thionyl chloride or phosphorus pentachloride; 2,2'-dipyridyl disulfide/triphenylphosphine; and the like, preferably isobutyl chloroformate), and treated with anhydrous ammonia in an anhydrous organic solvent (e.g., dioxane, tetrahydrofuran, and the like, preferably tetrahydrofuran), for from about 30 minutes to about 12 hours at from about −20° to about 40° C, preferably warming from about +15° to about 25° C during a 1 hour period, to give the compounds of Formula (4), β-benzyl t-butyloxycarbonyl-D-isoasparaginate ($n = 1$) or γ-benzyl t-butyloxycarbonyl-D-isoglutaminate ($n = 2$).

The $N^\alpha$-protecting group, as described above t-butyloxycarbonyl, is removed from the blocked isoasparagine β-benzyl ester or isoglutamine γ-benzyl ester compounds of Formula (4) procedures appropriate for the class of protecting group used and well known to those skilled in the art (e.g. by treatment with p-toluenesulfonic acid, methanesulfonic acid, hydrogen chloride, trifluoroacetic acid, formic acid, boron trifluoride or other moderately strong proton donors or electron acceptors, in an inert organic solvent, preferably a saturated solution of hydrogen chloride in ethyl acetate) by treatment for a period of from about 1 to about 69 minutes at from about −15° to about 40° C, preferably for about 15 to about 30 minutes at from about 15° to about 25° C, followed by dilution with a solvent of low dielectric constant (e.g., hexane, ether, benzene, and the like, preferable ether), to yield the compounds of Formula (5), β-benzyl isoasparaginate hydrochloride ($n = 1$) or γ-benzyl isoglutaminate hydrochloride ($n = 2$).

The t-butyloxycarbonyl compounds of Formula (6) are then reacted with the compounds of Formula (5) to give the compounds of Formula (7). This reaction is carried out in a polar solvent (ethyl acetate, acetonitrile, tetrahydrofuran, N,N-dimethylformamide and the like, preferably N,N-dimethylformamide) in the presence of a base (e.g., triethylamine, diisopropylethyl amine, N-methylmorpholine, and the like preferably diisopropylethylamine) and is brought about by the addition of suitable additives (e.g., the reagents described above for the preparation of the compounds of Formula (4), preferably dicyclohexylcarbodiimide /1-hydroxybenzotriazole), for a period of from about 30 minutes to about 40 hours at from about −10° to about 80° C, preferably from about 30 minutes to about 1 hour at about 10° to about 25° C to give the $N^\alpha$-protected dipeptide of Formula (7) wherein $n = 1$ or 2 and $X^1$ is defined as above. Alternatively other $N^{60}$-protecting groups are used instead of the t-butyloxycarbonyl group shown in Formula (6), for example, as described above for the preparation of compounds of Formula (3).

The N-acetylglycopeptides of Formula (13) (wherein $R = R^1 = H$ and $R^2 = CH_3$, $n = 1$ or 2 and X is as previously defined) are obtained as illustrated by the sequence of reactions proceeding from Formula (8) to Formula (13).

The starting material for this sequence is benzyl 2-acetamido-4,6-benzylidene-2-deoxy-α-D-glucopyranoside, Formula (8), the preparation of which has been described by P. H. Gross and R. W. Jeanloz in J. Org. Chem., 32, 2762 (1967). In addition, all of the subsequent steps can be performed equally well starting with the β-benzyl glycoside corresponding to Formula (8), the synthesis of which is also described in J. Org. Chem., 32, 2762 (1967). These steps are all carried out under conditions generally comparable to those described starting with the α-benzyl glycoside of Formula (8).

Alkylation of the free hydroxyl group of formula (8) is readily accomplished by first forming its anion with a suitable base such as sodium hydride, potassium hydride and the like in an inert organic solvent such as dimethylformamide, tetrahydrofuran, dioxane, and the like, at from about 0° to about 50° C, for from about 30 minutes to about 3 hours, and preferably in dimethylformamide at from about 10° to about 30° C, for from about 15 to about 60 minutes. The resulting anion is then reacted, preferably in the same solvent, with the anion of a haloacetic acid. This step is advantageously conducted in dimethylformamide at from about 20° to about 100° C, for from about 15 minutes to about 72 hours, and preferably at from about 50° to about 80° C, for from about 0.5 to about 2 hours, or from about 20° C to about 30° C from about 10 hours to about 48 hours. The resulting benzyl 2-acetamido-4,6-O-benzylidene-2-deoxy-3-O-carboxymethyl-α-D-glucopyranoside (9, $R^2 = CH_3$) is readily isolated in crystalline form.

The condensation of (9, $R^2 = CH_3$) with the various, suitably protected benzyl α-aminoacyl-D-isoglutaminate and benzyl α-aminoacyl-D-isoasparaginate derivatives of Formula (10) (wherein $X^1$ is L-alanyl, L-valyl, L-leucyl, L-isoleucyl, L-α-aminobutyryl, O-benzyl-L-seryl, O-benzyl-L-threonyl, L-methionyl, S-benzyl-L-cysteinyl, L-phenylalanyl, O-benzyl-L-tyrosyl, L-tryptophanyl, ε-carbobenzyloxy-L-lysyl, δ-carbobenzyloxy-L-ornithyl, gu-nitro-L-arginyl, $N^{Im}$-benzyl-L-histidyl, γ-benzyl ester of L-glutamyl, L-glutaminyl, β-benzyl ester of L-aspartyl, L-asparaginyl, L-prolyl and O-benzyl-L-hydroxyprolyl and $n = 1$ or 2) is conducted by various techniques familiar to one skilled in the art of peptide synthesis. Thus, for example, the dipeptide hydrochloride derivatives of Formula (10) are converted to the free base forms by addition of a suitable strongly basic tertiary amine such as diisopropylethylamine. The resulting free amino compound corresponding to a compound of Formula (10) is then condensed with the carbonyl group of a compound of Formula (9) (e.g., $R^2 = CH_3$) using, for example, a carbodiimide such as dicyclohexylcarbodiimide or diisopropylcarbodiimide in an inert organic solvent such as dimethylformamide, dichloromethane, ethyl acetate, dioxane, acetonitrile, and the like. Optionally, and preferably, the reaction is conducted in the presence of well known suitable additives such as 1-hydroxybenzotriazole, N-hydroxysuccinimide, p-nitrophenol, pentachlorophenol, and the like. We have found that condensations using dicyclohexylcarbodiimide and 1-hydroxybenzotriazole in dimethylformamide at from about 0° to about 50°C for from about 2 to about 48 hours, and preferably at from about 10 ° to about 30° C, for from about 10 to about 20 hours provide excellent results. The resulting products of Formula (11) (with $X^1$ and $n$ defined as above) are isolated and purified by conventional means including crystallization and chromatography on silicic acid. Alternatively, the condensation of the free bases of Formulas (10) and (9) can also be brought about by other methods familiar to the peptide art. Thus, for example, the use of mixed anhydrides derived from the compounds of Formula (9) in the presence of chloroformates (e.g., isobutylchloroformate) or 1-ethoxycarbonyl-2-ethoxy-1,2-dihydroquinoline are efficacious. Also, other types of carbonyl activation brought about, e.g., by the use of oxazolium salts or of triphenylphosphine in the presence of dipyridyldisulfide or carbon tetrahalides are useful. A general summary of such condensation methods is to be found in reviews by I. S. Klausner and M. Bodansky, Synthesis 453 (1972) and by J. H. Jones, Chemistry and Industry, 723 (1974).

The sequence of reactions in going from Formula (8) to Formula (9) can also be altered in such a way as to permit variation in the nature of the N-acyl function, $R^2CO$—. Thus, an N-acetyl function of Formula (8) can be hydrolyzed with strong base, as described in J. Org. Chem., 32, 2762 (1967), giving benzyl 2-amino-4,6-benzylidene-2deoxy-α-D-glucopyranoside, Formula (8A). This reaction can also be applied to the β-anomer of Formula (8) as also described in J. Org. Chem., 32 2762 (1967), and the resulting benzyl 2-amino-4,6-benzylidene-2-deoxy-β-D-glucopyranoside can be used in the subsequent reactions under essentially the same conditions as described starting with Formula (8A). Selective N-acylation of the compounds of Formula (8A) is brought about by reaction with carboxylic anhydrides in a lower alcohol, preferably methanol. The anhydrides include those from straight chain and branched aliphatic carboxylic acids, $R^2COOH$, in which $R^2$ contains 1 to 21 carbon atoms, optionally substituted with compatable substituents such as methoxy, benzyloxy, halogen (e.g., fluoro) or aryl groups, aryl groups containing up to 10 carbon atom and optionally substituted by lower alkyl, lower alkoxy or halogen groups. Thus, the acyl group $R^2CO$— encompasses such groups as formyl ($R^2$ = H, prepared by use of formic-acetic anhydride), acetyl, trifluoroacetyl, methoxyacetyl, butyryl, isobutyryl, valeryl, octanoyl, lauroyl, myristoyl, palmitoyl, behenoyl, phenylacetyl, benzoyl, p-fluorobenzoyl, p-methoxybenzoyl, naphthoyl, 7-methoxynaphthoyl, and the like. The exact conditions for the selective N-acylation depend upon the reactivity of the acid anhydride used. Generally, the reaction proceeds satisfactorily in methanol at from about 20° to about 65° C for periods of from about 15 minutes to about 6 hours and most of the reactions can also be conducted under reflux for from about 30 to about 60 minutes. In the case of certain highly reactive anhydrides, such trifluoroacetic anhydride, the reaction is preferably run using a slight excess of the anhydride in an inert solvent, such as tetrahydrofuran.

The compounds of Formula (8B) of the above reaction are then alkylated using sodium hydride and sodium chloroacetate in dimethylformamide, as described above, giving the varied benzyl 2-acylamido-4,6-O-benzylidene-3-O-carboxymethyl-α-D-glucopyranosides of Formula (9) with $R^2CO$—, defined as above. Coupling of these derivatives with the free base derived from Formula (10) is achieved by the same methods described above for the obtention of the compounds of Formula (9, $R^2$ = $CH_3$) and giving the blocked glycopeptides of Formula (11) in which the acyl group $R^2CO$—, the aminoacyl group $X^1$ and n are defined as above.

The removal of the protecting groups from the blocked glycopeptides of Formula (11) is achieved by catalytic hydrogenolysis, using a suitable palladium catalyst. This reaction is normally conducted in an acidic medium under a pressure of 1-2 atmospheres of hydrogen at close to room temperature using 5-10% palladium on charcoal, palladium on barium sulfate, palladium black or related catalysts. Preferably a palladium on charcoal catalyst in about 60 to about 90% aqueous acetic acid is used. Under these conditions the removal of all protecting groups is complete within from about 24 to about 72 hours, and can be, if desired, monitored by thin-layer chromatography, thus resulting in the glycodipeptide products (e.g., 2-acetamido-2-deoxy-D-glucos-3-O-yl-acetyl-L-alanyl-D-isoglutamine) of Formula (13, R = $R^1$ = H, $R^2CO$— is as previously defined, except that when $R^2$ in Formula (11) is benzyloxymethyl the benzyl ether is simultaneously cleaved giving the compounds of Formula (13) wherein $R^2$ is hydroxymethyl, and X is L-alanyl,L-valyl, L-leucyl, L-isoleucyl, L-α-aminobutyryl, L-seryl, L-threonyl, L-methionyl, L-cysteinyl, L-phenylalanyl, L-tyrosyl, L-tryptophanyl, L-lysyl, L-ornithyl, L-arginyl, L-histidyl, L-glutamyl, L-glutaminyl, L-aspartyl, L-asparaginyl, L-prolyl or L-hydroxyprolyl). These compounds are purified by conventional chromatographic techniques such as chromatography on a column of BIOREX 70 (a weakly acidic polyacrylic acid resin). On occasion this chromatography alone does not completely remove minor impurities. In those cases passage through a column of Dowex 50 ($H^+$), a sulfonated polystyene crosslinked with divinylbenzene resin, will effectively remove basic impurities, or chromatography on a column of Amberlite XAD-2 (polystyrene crosslinked with 2% divinylbenzene) in water or aqueous methanol will separate any partially deblocked glycopeptide.

A further aspect of this invention relates to the synthesis of 4,6-di-O-acyl derivatives of the glycodipeptides of Formula (13), in which R and $R^1$ are the same or different acyl radicals, and X, $R^2$ and n are as previously defined.

The preferred acyl radicals are these containing straight or branched chain alkyl, aralkyl, alkaryl, or aryl radicals containing from 1 to 21 carbon atoms, e.g., acetyl, butyryl, isovaleryl, hexanoyl, octanoyl, lauroyl, myristoyl, palmitoyl, stearoyl, behenoyl, benzoyl, p-toluoyl, phenylacetyl, naphthoyl, and the like.

In addition, we have developed selective syntheses of the 4-O- and 6-O-acyl derivatives of Formula (13) in which one of R or $R^1$ is an acyl radical defined as above while the other group ($R^1$ or R) is hydrogen and X, $R^2$ and n are as previously defined.

The syntheses of all three types of compound use, as their initial step, the selective acidic hydrolysis of the 4,6-O benzylidene function from the protected glycopeptide of Formula (11) in which $X^1$, $R^2$ and n are as previously defined. This hydrolysis is carried out using a variety of acidic treatments familiar to the art of carbohydrate chemistry. These include treatment with 50–90% acetic, formic or propionic acids at from about 50° to about 100° C., or brief treatment with strong acids such as about 90% trifluoroacetic acid at room temperature. Advantageously, the reaction is done using about 60% to about 80% acetic acid at about 100° for about 5 to about 8 minutes. Following a conventional work-up, the otherwise fully protected 4,6-diol of Formula (12A) is isolated and purified by crystallization or chromatography on a suitable absorbent such as silicic acid.

Acylation of both free hydroxyl groups of Formula (12A) is achieved by treatment with two or more molar equivalents of a conventionally activated acylating agent such as an acyl anhydride, acyl chloride, acyl cyanide or acyl imidazolide in a suitable inert organic solvent in the presence of a tertiary base. Suitable solvents include pyridine, methylene chloride, acetonitrile, dimethylformamide, tetrahydrofuran, dioxane and the like, while pyridine, triethylamine, N-methylmorpholine, diisoproylethylamine, and the like, are suitable bases. The use of 2–10 molar equivalents of either the acyl chloride or acyl anhydride in pyridine at room temperature for from about 10 to about 24 hours is generally advantageous and the resulting 4,6-di-O-acyl derivatives of Formula (12E), in which $R^4$ and $R^5$ are identical acyl radicals defined in the same way as R and $R^1$, are isolated and purified by crystallization or chromatography on an absorbent such as silicic acid. Removal of protecting groups from the compounds of Formula (12E) is accomplished by catalytic hydrogenolysis using a palladium derived catalyst as previously described for the conversion of the compounds of Formula (11) to the compounds of Formula (13), wherein R and $R^1$ are hydrogen. The resulting products are those of Formula (13), in which R and $R^1$ are identical acyl groups, $R^2$, X and $n$ are as previously defined, except that $R^2$ also includes hydroxymethyl.

Alternatively, acylation of the compounds of Formula (12A) using only a slight excess (about 1.0 to 1.2 molar equivalents) of an acyl anhydride, acyl chloride, acyl cyanide or acyl imidazolide in an inert organic solvent containing a tertiary base, as above, produces selective acylation of the primary 6-hydroxyl group. This reaction is preferably conducted by the gradual addition of the acylating agent to a solution of a compound of Formula (12A) at from about 0° to about 20° C and is monitored by thin-layer chromatography until the starting material is essentially consumed. Following a conventional work-up, the 6-O-acyl derivative of Formula (12F), in which $R^3$ is an acyl group defined identically to R and $R^1$ and $X^1$, $n$ and $R^2$ are as previously defined, are isolated and purified by chromatography on a suitable absorbent such as silicic acid or by crystallization. Catalytic hydrogenolysis of the compounds of Formula (12F) is carried out as previously described using a palladium derived catalyst giving compounds of Formula (13), wherein R and $R^2CO-$ are acyl radicals as previously defined, except that benzyloxyacetyl is replaced by a hydroxyacetyl (glycolyl) moiety, and $R^1$ is hydrogen.

To introduce an acyl group selectively at the 4-O position it is necessary to first selectively introduce a protecting group on the $C_6$-hydroxy group of Formula (12A). This can conveniently be done by the use of a trityl or substituted trityl ether, a technique well known in carbohydrate chemistry. Thus the compounds of Formula (12A) are reacted with triphenylmethyl chloride (trityl chloride) or with related reagents such as anisyldiphenylmethyl chloride (methoxytrityl chloride), dianisylphenymethyl chloride (dimethyoxytrityl chloride) or trianisylmethyl chloride (trimethoxytrityl chloride) in pyridine or in inert solvents such as dimethylformamide, dimethyl sulfoxide, acetonitrile and the like, containing pyridine. [See e.g., M. Smith et al., J. Amer. Chem Soc., 84,430 (1962) for representative use of these reagents.] In general, the reactions can be conducted at from about 10° to about 50° C, and advantageously in pyridine at room temperature. The length of time of the reaction depends upon the reagent used and varies from about 2 to about 5 hours with trianisylmethyl chloride to about from 3 to about 6 days for triphenylmethyl chloride. The resulting 6-O-trityl or substituted 6-O-trityl ethers of Formula (12B) are readily isolated by conventional techniques such as precipitation, crystallization or chromatography on a suitable absorbent such as silicic acid. In Formula (12B), $X^1$, $n$ and $R^2CO-$ are as previously defined.

Acylation of the free 4-hydroxyl group of Formula (12B) is done using conventional acylating agents such as acyl chlorides, acyl anhydrides, acyl cyanides or acyl imidazolides derived from acids, in which the acyl moiety, $R^3$, is defined as above. The reaction can be conducted under the same conditions described for the acylation of the compounds of Formula (12A) to give the compounds of Formula (12E) except that the molar ratio of acylating agent is optionally as low as from about 1 to about 5 equivalents. The resulting acylated products of Formula (12C), in which $R^2$, $R_3$, $X^1$ and $n$ are as previously defined, are isolated and purified by crystallization, precipitation or chromatography on a suitable absorbent such as silicic acid.

Selective hydrolysis of the trityl (or substituted trityl) group can be brought about under defined acidic conditions. This is advantageously done by treatment with 70% acetic acid at 100° C until a clear solution results and then for about a further 2 minutes. These conditions can be modified with respect to temperature, time and acidic strength by one skilled in the art but excessive conditions are to be avoided. If the methoxytrityl derivatives corresponding to Formula (12C) are used the conditions for acidic hydrolysis are much milder and the use of 80% acetic acid at room temperature for from about 5 minutes to about 5 hours is sufficient. The resulting 4-O-acyl derivatives of Formula (12D), in which $X^1$, $n$, $R^3$ and $R^2$ are as previously defined, are isolated and purified by crystallization or chromatography on silicic acid.

Further acylation of the 6-hydroxyl group in the compounds of Formula (12D) is achieved using acylating agents derived from the carboxylic acids, $R^4OH$ under the conditions outlined for the preparation of compounds of Formulas (12E) or (12C). The resulting products of Formula (12E), in which the acyl radicals $R^4$ and $R^5$ are either the same or different as previously defined, and $R^2$, $X^1$, and $n$ are as previously defined, can be isolated and purified by conventional techniques.

Alternatively, the compounds of Formula (12E) are prepared by further acylation of the compounds of Formula (12F) using acylating agents derived from the acids $R^5OH$, as previously described. Once again, the resulting compounds of Formula (12E), in which the acyl groups $R^4$ and $R^5$ are either the same or different as previously defined, and $R^2$, $X^1$, and $n$ are as previously defined, are isolated and purified by conventional means.

Removal of protecting groups from the compounds of Formulas (12D), (12E) and (12F) is achieved by catalytic hydrogenolysis using palladium derived catalysts in an acidic medium as previously described for the conversion of the compounds of Formula (12A) to the compounds of Formula (13). The resulting products are the compounds of Formula (13) in which X, $n$ and $R^2CO-$ are as previously defined and R and $R^1$ are the same or different acyl groups or either R or $R^1$ are hydrogen while the other is an acyl group. In any case the acyl groups R, $R^1$ and $R^2CO-$ are as previously defined, except that the benzyloxyacetyl group is replaced by the hydroxyacetyl (glycolyl) group. These compounds of Formula (13) are isolated by precipitation from methanol by addition of a less polar solvent, such as ethyl acetate or ether, and then further purified by chromatography on BIOREX 70 or Amberlite XAD-2 resins as previously described for the conversion of the compounds of Formula (12A) to the compounds of Formula (13). Clearly other chromatographic techniques well known to the peptide and glycopeptide art could be alternatively employed for these purifications.

It is to be understood that isolation of the compounds described herein can be effected, if desired, by any suitable separation or purification procedure, such as, for example, extraction, crystallization, thin-layer chromatography, thick-layer chromatography or column chromatography, or a combination of these procedures. Illustrations of suitable separation and isolation procedures can be had by reference to the Examples herein below. However, other equivalent separation or isolation procedures could, of course, also be used.

By the term room temperature is meant a temperature of from about 15° to about 25° C.

A further understanding of the invention can be had from the following non-limiting Examples.

EXAMPLE 1

50 Ml. of concentrated sulfuric acid is added cautiously to 500 ml of anhydrous ether, and to this mixture is then added 500 ml of benzyl alcohol. The ether is removed by evaporation in vacuo and to the residue there is added during 0.5 hours 67 g of D-aspartic acid (1, $n = 1$) in several portions. The resulting suspension is stirred at 22° C for 16 hours to give a clear solution. To this vigorously stirred solution there is added one 1 of 95% ethanol and 250 ml of pyridine. After a few minutes crystallization commences and the mixture is stored at 0° C for 20 hours. The product is collected by filtration and is washed thoroughly with ether to give 77.9 g of a white solid having a melting point of 172°–177° C, which is recrystallized from one 1 of water containing 10 drops of pyridine to give 44.3 of β-benzyl D-aspartate (2, $n = 1$) having a melting point of 220°–221° C and an $[\alpha]_D^{25} -28.1°$ (10 mg/ml, 1N hydrochloric acid).

In like manner substituting a stoichiometric equivalent amount of D-glutamic acid (1, $n = 2$), for D-aspartic acid, there is obtained 56.3 g of γ-benzyl D-glutamate (2, $n = 2$) having a melting point of 161°–162° C and an $[\alpha]_D^{25} -19.3°$ (6 mg/ml, acetic acid).

EXAMPLE 2

In a 500 ml round bottomed flask there is placed 250 ml of anhydrous dimethylsulfoxide, 11.15 g of β-benzyl D-aspartate (2, $n = 1$), 13.5 ml of triethylamine and 9 ml of t-butylazidoformate and the resulting solution is stored at 22° C for 42 hours. The reaction mixture is then poured into 700 ml of water and the mixture is extracted three times with 200 ml of ether. The aqueous layer is cooled in ice, 200 ml of ethyl acetate is added and the aqueous phase is brought to pH 2.8 by the addition of citric acid. The layers are separated and the aqueous phase is further extracted three times with 200 ml of ethyl acetate. The combined organic phase is extracted successively five times with 200 ml of water, with 200 ml of saturated brine and is then dried over magnesium sulfate. The ethyl acetate solution is filtered and the filtrate is evaporated to dryness to give a solid residue which is crystallized from ethyl acetate-hexane to give 13.2 g of β-benzyl t-butyloxycarbonyl-D-aspartate (3, $n = 1$) having a melting point of 102°–103° C; $[\alpha]_D^{25} + 19.4°$ (14 mg/ml, dimethylformamide);

Anal. Calcd. for $C_{16}H_{21}NO_6$ (323.34): C, 59.43; H, 6.55; N, 4.33. Found: C, 59.51; H, 6.39; N, 4.28.

In like manner substituting a stoichiometric equivalent amount of γ-benzyl D-glutamate (2, $n = 2$) for β-benzyl D-aspartate there is obtained 16.9 g of γ-benzyl t-butyloxycarbonyl-D-glutamate (3, $n = 2$) as a pale yellow oil which is pure enough to be used directly in the next step.

EXAMPLE 3

A magnetically stirred solution of 3.23 g of β-benzyl t-butyloxycarbonyl-D-aspartate (3, $n = 1$) and 1.6 ml of triethylamine in 20 ml of tetrahydrofuran is cooled to $-15°$ C. A solution of 1.55 ml of isobutyl chloroformate in 5 ml of tetrahydrofuran is added dropwise to the above solution and the temperature is maintained at $-15°$ C for 25 minutes. Dry ammonia gas is then bubbled into the reaction mixture while the temperature is maintained at $-15°$ C for 30 minutes. The temperature of the reaction mixture is then allowed to rise to 0° C over 15 minutes, at which time the passage of ammonia gas is discontinued. The tetrahydrofuran is evaporated in vacuo and the residue is partitioned between 80 ml of water and 200 ml of ethyl acetate. The ethyl acetate layer is washed successively twice with 50 ml of 5% aqueous sodium bicarbonate solution and with 50 ml of saturated brine and is then dried over magnesium sulfate. The filtered solution is evaporated to dryness to give 3.22 g of a solid which is recrystallized from 50 ml of ethyl acetate to give 2.72 g of benzyl t-butyloxycarbonyl-D-isoasparaginate (4, $n = 1$) having a melting point of 159°–160° C; $[\alpha]_D^{25} + 17.0°$ (10 mg/ml, dimethylformamide);

Anal. Calcd. for $C_{16}H_{22}N_2O_5$ (322.35): C, 59.61; H, 6.88; N, 8.69. Found: C, 59.81; H, 6.80; N, 8.87.

In like manner substituting a stoichiometric equivalent amount of γ-benzyl t-butyloxycarbonyl-D-glutamate (3, $n = 2$) for β-benzyl t-butyloxycarbonyl-D-aspartate there is obtained 1.92 g of benzyl t-butyloxycarbonyl-D-isoglutaminate (4, $n = 2$) having a melting point of 125°–126° C; $[\alpha]_D^{25} - 2.6°$ (13.3 mg/ml, dimetylformamide).

EXAMPLE 4

A. To 2.95 g of benzyl t-butyloxycarbonyl-D-isoglutaminate (4, $n = 2$) there is added 14 ml of a saturated solution of hydrogen chloride in ethyl acetate. The reaction mixture is stored at 22° C for 10 minutes and then 80 ml of ether is added to precipitate the product, which is collected by centrifugation and carefully dried in vacuo to give 2.33 g of γ-benzyl D-isoglutaminate hydrochloride (5, $n = 2$) which is used without further purification in step B of this example.

B. To 2.01 g of t-butyloxycarbonyl-L-alanine (6, $X^1$ = L-alanyl) dissolved in 10 ml. of dry dimethylformamide there is added 1.72 g of 1-hydroxybenzotriazole and 2.19 g of dicyclohexylcarbodiimide. The resulting mixture is kept at 22° C for 1.5 hours and is then filtered into a solution of 2.33 g of γ-benzyl D-isoglutaminate hydrochloride (5, $n = 2$) and 1.55 ml of diisopropylethylamine in 10 ml of dimethylformamide. The insoluble cake resulting from this filtration is washed twice with 5 ml. of dimethylformamide and the washings are added to the reaction mixture, which is stored at 22° C for 1 hour. The reaction mixture is poured into 500 ml of water and the resulting solution is extracted twice with 250 ml of ethyl acetate. The combined organic phases are washed successively four times with 200 ml of water, three times with 150 ml of 5% aqueous potassium bicarbonate solution and with 150 ml of saturated brine. The ethyl acetate solution is then dried over magnesium sulfate, filtered and evaporated to dryness to yield a solid residue which is crystallized from a mixture of ethanol and ether to give 2.2 g of benzyl t-butyloxycarbonyl-L-alanyl-D-isoglutaminate (7, $n = 2$, $X^1$ = L-alanyl) having a melting point of 140°–141° C; $[\alpha]_D^{25} 0°$ (7.6 mg/ml, dimethylformamide);

Anal. Calcd, for $C_{20}H_{29}N_3O_6$ (407.45): C, 58.95; H, 7.17; N, 10.31. Found: C, 59.11; H, 6.80; N, 10.50.

In like manner substituting a stoichiometric equivalent amount of
t-butyloxycarbonyl-L-valine,
t-butyloxycarbonyl-L-leucine, t-butyloxycarbonyl-L-isoleucine,
t-butyloxycarbonyl-L-α-aminobutyric acid,
t-butyloxycarbonyl-O-benzyl-L-serine,
t-butyloxycarbonyl-O-benzyl-L-threonine,
t-butyloxycarbonyl-L-methionine,
t-butyloxycarbonyl-S-benzyl-L-cysteine,
t-butyloxycarbonyl-L-phenylalanine,
t-butyloxycarbonyl-O-benzyl-L-tyrosine,
t-butyloxycarbonyl-L-tryptophan,
t-butyloxycarbonyl-ε-carbobenzyloxy-L-lysine,
t-butyloxycarbonyl-γ-carbobenzyloxy-L-ornithine,
t-butyloxycarbonyl-gu-nitro-L-arginine,
t-butyloxycarbonyl-N$^{Im}$-benzyl-L-histidine,
γ-benzyl t-butyloxycarbonyl-L-glutamate,
t-butyloxycarbonyl-L-glutamine,
β-benzyl t-butyloxycarbonyl-L-aspartate,
t-butyloxycarbonyl-L-asparagine,
t-butyloxycarbonyl-L-proline, and
t-butyloxycarbonyl-O-benzyl-L-hydroxyproline,
for t-butyloxycarbonyl-L-alanine, there are obtained the corresponding protected dipeptide derivatives, benzyl t-butyloxycarbonyl-L-valyl-D-isoglutaminate having a melting point of 152°–153° C; $[\alpha]_D^{25}$ + 9.1° (10 mg/ml, dimethylformamide;)

Anal. Calcd. for $C_{22}H_{33}N_3O_6$ (435.50): C, 60.67; H, 7.64; N, 9.65. Found: C, 60.88; H, 7.90; N, 9.67.

benzyl t-butyloxycarbonyl-L-leucyl-D-isoglutaminate having a melting point of 105°–106° C;

benzyl t-butyloxycarbonyl-L-isoleucyl-D-isoglutaminate, benzyl t-butyloxycarbonyl-L-α-aminobutyryl-D-isoglutaminate, benzyl t-butyloxycarbonyl-O-benzyl-L-seryl-D-isoglutaminate having a melting point of 64°–66° C; $[\alpha]_D^{25}$ + 1.0° (8.2 mg/ml, dimethylformamide);

Anal. Calcd. for $C_{27}H_{35}N_3O_7$ (513.57): C, 63.14; H, 6.87; N, 8.18. Found: C, 63.41; H, 6.92; N, 8.29, benzyl t-butyloxycarbonyl-O-benzyl-L-threonyl-D-isoglutaminate, having a melting point of 117°–120° C; $[\alpha]_D^{25}$ + 7.1° (5.0 mg/ml, dimethylformamide);

Anal. Calcd. for $C_{28}H_{37}N_3O_7$ (527.63): C, 63.74; H, 7.07, N, 7.96. Found: C, 63.59; H, 6.81; N, 7.84, benzyl t-butyloxycarbonyl-L-methionyl-D-isoglutaminate having a melting point of 114°–115° C; $[\alpha]_D^{25}$ + 25° (10 mg/ml, dimethylformamide):

Anal. Calcd. for $C_{22}H_{33}N_3O_6S$ (467.59): C, 56.51; H, 7.11; N, 8.99. Found: C, 56.59; H, 7.24; N, 8.93, benzyl t-butyloxycarbonyl-S-benzyl-L-cysteinyl-D-isoglutaminate, benzyl t-butyloxycarbonyl-L-phenylalanyl-D-isoglutaminate, having a melting point of 139° C–140° C, benzyl t-butyloxycarbonyl-O-benzyl-L-tyrosyl-D-isoglutaminate having a melting point of 172°–173° C; $[\alpha]_D^{25}$ + 4.2° (4.6 mg/ml, dimethylformamide);

Anal. Calcd. for $C_{33}H_{39}N_3O_7$ (589.66): C, 67.21; H, 6.67; N, 7.13. Found: C, 67.44; H, 6.88, N, 7.06, benzyl t-butyloxycarbonyl-L-tryptophanyl-D-isoglutaminate, benzyl t-butyloxycarbonyl-ε-carbobenzyloxy-L-lysyl-D-isoglutaminate having a melting point of 94°–97° C; $[\alpha]_D^{25}$ −3.5° (8 mg/ml, dimethylformamide);

Anal. Calcd. for $C_{31}H_{42}N_4O_8$ (598.68): C, 62.19; H, 7.07; N, 9.36. Found: C, 62.19; H, 7.03; N, 9.44, benzyl t-butyloxycarbonyl-δ-carbobenzyloxy-L-ornithyl-D-isoglutaminate, benzyl t-butyloxycarbonyl-gu-nitro-L-arginyl-D-isoglutaminate, benzyl t-butyloxycarbonyl-N$^{Im}$-benzyl-L-histidyl-D-isoglutaminate, benzyl t-butyloxycarbonyl-γ-benzyl-L-glutamyl-D-isoglutaminate, benzyl t-butyloxycarbonyl-L-glutaminyl-D-isoglutaminate, benzyl t-butyloxycarbonyl-β-benzyl-L-aspartyl-D-isoglutaminate, benzyl t-butyloxycarbonyl-L-asparaginyl-D-isoglutaminate, benzyl t-butyloxycarbonyl-L-prolyl-D-isoglutaminate, a colorless oil having $[\alpha]_D^{25}$ −9.0° (14.4 mg/ml, dimethylformamide);

Anal. Calcd. for $C_{22}H_{31}N_3O_6$ (433.49): C, 60.95; H, 7.21; N, 9.69. Found: C, 61.06; H, 7.49; N, 9.85, and benzyl t-butyloxycarbonyl-O-benzyl-L-hydroxyprolyl-D-isoglutaminate.

In like manner substituting a stoichiometric equivalent amount of benzyl t-butyloxycarbonyl-D-isoasparaginate hydrochloride (4, n = 1) for benzyl t-butyloxycarbonyl-D-isoglutaminate hydrochloride (4, n = 2) there are obtained the corresponding protected dipeptide derivatives, benzyl t-butyloxycarbonyl-L-alanyl-D-isoasparaginate having a melting point of 126°–127° C; $[\alpha]_D^{25}$ −6.4° (10 mg/ml, dimethylformamide);

Anal. Calcd. for $C_{19}H_{27}N_3O_6$ (393.43): C, 58.00; H, 6.92; N, 10.68. Found: C, 57.98; H, 7.10; N, 10.66, benzyl t-butyloxycarbonyl-L-valyl-D-isoasparaginate, benzyl t-butyloxycarbonyl-L-leucyl-D-isoasparaginate, benzyl t-butyloxycarbonyl-L-isoleucyl-D-isoasparaginate, benzyl t-butyloxycarbonyl-L-α-aminobutyryl-D-isoasparaginate, benzyl t-butyloxycarbonyl-O-benzyl-L-seryl-D-isoasparaginate, benzyl t-butyloxycarbonyl-O-benzyl-L-threonyl-D-isoasparaginate, benzyl t-butyloxycarbonyl-L-methionyl-D-isoasparaginate, benzyl t-butyloxycarbonyl-S-benzyl-L-cysteinyl-D-isoasparaginate, benzyl t-butyloxycarbonyl-L-phenylalanyl-D-isoasparaginate, benzyl t-butyloxycarbonyl-O-benzyl-L-tyrosyl-D-isoasparaginate, benzyl t-butyloxycarbonyl-L-tryptophanyl-D-isoasparaginate, benzyl t-butyloxycarbonyl-ε-carbobenzyloxy-L-lysyl-D-isoasparaginate, benzyl t-butyloxycarbonyl-δ-carbobenzyloxy-L-ornithyl-D-isoasparaginate, benzyl t-butyloxycarbonyl-gu-nitro-L-arginyl-D-isoasparaginate, benzyl t-butyloxycarbonyl-N$^{Im}$-benzyl-L-histidyl-D-isoasparaginate, benzyl t-butyloxycarbonyl-γ-benzyl-L-glutamyl-D-isoasparaginate, benzyl t-butyloxycarbonyl-L-glutaminyl-D-isoasparaginate, benzyl t-butyloxycarbonyl-β-benzyl-L-aspartyl-D-isoasparaginate, benzyl t-butyloxycarbonyl-L-asparagine-D-isoasparaginate, benzyl t-butyloxycarbonyl-L-prolyl-D-isoasparaginate, and benzyl t-butyloxycarbonyl-O-benzyl-L-hydroxyprolyl-D-isoasparaginate.

EXAMPLE 5

A. A solution of 3.57 g of benzyl 2-amino-4,6-O-benzylidene-2-deoxy-α-glucopyranoside (8A) and 2.49 g of benzoic anhydride in 200 ml of methanol is heated under reflux for 45 minutes. The resulting mixture is allowed to cool to 22° C and the crystalline solid is collected by filtration, washed with methanol and recrystallized from hot methanol to yield 3.46 g of benzyl 2-benzamido-4,6,-O-benzylidene-2-deoxy-α-D-glucopyranoside (8B, $R^2$ = Ph) having a melting point of 218°–220° C; $[\alpha]_D^{25}$ + 119° (10 mg/ml, pyridine);

Anal. Calcd. for $C_{27}H_{27}NO_6 \cdot H_2O$ (479.54): C, 67.63; H, 6.10; N, 2.92. Found: C, 68.09; H, 5.81; N, 2.87.

B. A solution of 3.57 g of benzyl 2-amino-4,6-O-benzylidene-2-deoxy-α-D-glucopyranoside (8A) and 2.31 g of trifluoroacetic anhydride in 100 ml of tetrahydrofuran is heated under reflux for 1 hour. The resulting solution is allowed to cool to about room temperature and is then added to one 1 of ice water. The precipitated solid is collected by filtration, washed thoroughly with water and dried in vacuo giving 4.51 g of benzyl 4,6-O-benzylidene-2-deoxy-2-trifluoroacetamido-α-D-glucopyranoside having a melting point of 242°–243° C.

C. A solution of 5.4 g of benzyl 2-amino-4,6-O-benzylidine-2-deoxy-α-D-glucopyranoside (8A) and 2.7 g of methoxyacetic anhydride in 250 ml of methanol is heated under reflux for 30 minutes. The resulting solution is then concentrated in vacuo and the residue is triturated with 150 ml of ether giving, after filtration, 5.99 g of benzyl 4,6-O-benzylidene-2-deoxy-2-methoxyacetamido-α-D-glucopyranoside (8B, $R^2$ = —CH$_2$OCH$_3$) having a melting point of 198°–199° C; $[\alpha]_D^{25}$ + 82.0° (10 mg/ml, chloroform);

Anal. Calcd. for $C_{23}H_{27}NO_7$ (429.47): C, 64.32: H, 6.34; N, 3.26 Found: C, 64.19; H, 6.28; N, 3.06.

In like manner substituting a stoichiometric equivalent amount of the appropriate acylating agent for benzoic anhydride and using modified procedure B or C depending upon the physical properties of the product there are obtained the corresponding 2-acylamino glucose derivatives of Formula (8B):

benzyl 2-formamido-4,6-O-benzylidene-2-deoxy-α-D-glycopyranoside,
benzyl 2-propionamido-4,6-O-benzylidene-2-deoxy-α-D-glucopyranoside,
benzyl 2-butyramido-4,6-O-benzylidene-2-deoxy-α-D-glucopyranoside,
benzyl 2-valeramido-4,6-O-benzylidene-2-deoxy-α-D-glucopyranoside,
benzyl 2-caproamido-4-6-O-benzylidene-2-deoxy-α-D-glucopyranoside,
benzyl 2-heptanamido-4,6-O-benzylidene-2-deoxy-α-D-glucopyranoside,
benzyl 2-caprylamido-4,6-O-benzylidene-2-deoxy-α-D-glucopyranoside,
benzyl 2-nonanamido-4,6-O-benzylidene-2-deoxy-α-D-glucopyranoside,
benzyl 2-capramido-4,6-O-benzylidene-2-deoxy-α-D-glucopyranoside,
benzyl 2-lauramido-4,6-O-benzylidene-2-deoxy-α-D-glucopyranoside,
benzyl 2-myristamido-4,6-O-benzylidene-2-deoxy-α-D-glucopyranoside,
benzyl 2-palmitamido-4,6-O-benzylidene-2-deoxy-α-D-glucopyranoside,
benzyl 2-stearamido-4,6-O-benzylidene-2-deoxy-α-D-glucopyranoside,
benzyl 2-arachidamido-4,6-O-benzylidene-2-deoxy-α-D-glucopyranoside,
benzyl 2-behenamido-4,6-O-benzylidene-2-deoxy-α-D-glucopyranoside,
benzyl 2-benzyloxyacetamido-4,6-O-benzylidene-2-deoxy-α-D-glucopyranoside, and
benzyl 2-phenylacetamido-4,6-O-benzylidene-2-deoxy-α-D-glucopyranoside.

EXAMPLE 6

To a solution of 41.7 g of benzyl 2-acetamido-4,6-O-benzylidene-2-deoxy-α-D-glucopyranoside (8) in 500 ml of dry dimethylformamide there is added portionwise 19.2 g of a 50% dispersion of sodium hydride in oil. The resulting mixture is stirred at 22° C for 30 minutes, then 23.3 g of sodium chloroacetate is added and the reaction mixture is heated at 75° C for 1 hour. The reaction mixture is cooled in an ice-water bath, 125 ml of ethanol is added dropwise until the foaming subsides (about 30 minutes) and the resulting solution is evaporated to dryness in vacuo. The thus obtained residue is mechanically stirred with a mixture of 500 ml of chloroform and 500 ml of water until the sodium salt of the product crystallizes. The crystals are collected by filtration, resuspended in 3 l of chloroform and approximately 450 ml of Dowex 50 (H$^+$) (sulfonated polystyrene resin cross linked with divinyl benzene) is added and the mixture is stirred at 22° C for 1 hour. The resin is removed by filtration, the chloroform filtrate is dried over magnesium sulfate, refiltered and evaporated to dryness in vacuo to give 30 g of benzyl 2-acetamido-4,6-O-benzylidene-2-deoxy-3-O-carboxymethyl-α-D-glucopyranoside (9, $R^2$ = CH$_3$) having a melting point of 215°–216° C.

In like manner substituting a stoichiometric equivalent amount of the various compounds obtained in Example 5 for benzyl 2-acetamido-4,6-O-benzylidene-2-deoxy-α-D-glucopyranoside there are obtained the corresponding compounds of Formula (9).

EXAMPLE 7

A. To 0.406 g of benzyl t-butyloxycarbonyl-L-alanyl-D-isoglutaminate (7, n = 2, $X^1$ = L-alanyl) at 22° C there is added 5 ml of a saturated solution of hydrogen chloride in ethyl acetate. After 10 minutes, 40 ml of ether is added and the precipitated salt is collected by centrifugation and carefully dried in vacuo to give 0.325 g of benzyl L-alanyl-D-isoglutaminate hydrochloride (10, n = 2, $X^1$ = L-alanyl).

B. To a solution of 0.325 g of benzyl L-alanyl-D-isoglutaminate hydrochloride, (10, n = 2, $X^1$ = L-alanyl) in 5 ml of dimethylformamide there is added 0.17 ml of diisopropylethylamine followed by a solution of 0.227 g of dicyclohexylcarbodiimide, 0.178 g of 1-hydroxybenzotriazole and 0.512 g of benzyl 2-acetamido-4,6-O-benzylidene-2-deoxy-3-O-carboxymethyl-α-D-glucopyranoside (9, $R^2$ = CH$_3$) in 5 ml of dimethylformamide. The resulting reaction mixture is magnetically stirred at 22° C for 16 hours and then the insoluble N,N'-dicyclohexylurea is removed by filtration. The filtrate is diluted with 150 ml of ethyl acetate and the resulting solution is poured into 100 ml of water. The ethyl acetate phase is separated and washed successively twice with 150 ml of water, twice with 100 ml of 1N hydrochloric acid, with 100 ml of water, twice with 100 ml of 5% aqueous potassium bicarbonate solution and 100 ml of saturated brine, and is dried over magnesium sulfate. The drying agent is removed by filtration and the filtrate is evaporated to dryness to give a gel which is purified by crystallization from 60 ml of ethanol to give 0.68 g of benzyl (benzyl 2-acetamido-4,6-O-benzylidene-2-deoxy-α-D-glucopyranosid-3-O-yl)-acetyl-L-alanyl-D-isoglutaminate (11, $n = 2$, $X^1 =$ L-alanyl, $R^2 = CH_3$) having a melting point of 223°–224° C; $[\alpha]_D^{24} + 76.9°$ (2.6 mg/ml, dimethylformamide);

Anal. Calcd. for $C_{39}H_{46}N_4O_{11}$ (746.79): C, 62.72; H, 6.21; N, 7.50. Found: C, 62.57; H, 6.51; N, 7.32.

In like manner substituting a stoichiometric equivalent amount of the various products from Example 4, for benzyl t-butyloxycarbonyl-L-alanyl-D-isoglutaminate, there are obtained the corresponding protected glycopeptide derivatives, benzyl (benzyl 2-acetamido-4,6-O-benzylidene-2-deoxy-α-D-glucopyranosid-3-O-yl)-acetyl-L-valyl-D-isoglutaminate having a melting point of 237°–239° C; $[\alpha]_D^{25} + 80.9°$ (9 mg/ml, dimethylformamide);

Anal. Calcd. for $C_{41}H_{50}N_4O_{11}$ (774.84): C, 63.55; H, 6.50; N, 7.23. Found: C, 63.45; H, 6.51; N, 7.06, benzyl (benzyl 2-acetamido-4,6-O-benzylidene-2-deoxy-α-D-glucopyranosid-3-O-yl)-acetyl-L-leucyl-D-isoglutaminate, having a melting point of 209°–211° C;

Anal. Calcd. for $C_{42}H_{52}N_4O_{11}$ (788.91): C, 63.94; H, 6.64; N, 7.10. Found: C, 63.72; H, 6.59; N, 6.95, benzyl (benzyl 2-acetamido-4,6-O-benzylidene-2-deoxy-α-D-glucopyranosid-3-O-yl)-acetyl-L-isoleucyl-D-isoglutaminate, benzyl (benzyl 2-acetamido-4,6-O-benzylidene-2-deoxy-α-D-glucopyranosid-3-O-yl)-acetyl-L-α-aminobutyrly-D-isoglutaminate, benzyl (benzyl 2-acetamido-4,6-O-benzylidene-2-deoxy-α-D-glucopyranosid-3-O-yl)-acetyl-O-benzyl-L-seryl-D-isoglutaminate having a melting point of 211°–214° C; $[\alpha]_D^{23} + 69.3°$ (4.6 mg/ml, dimethylformamide);

Anal. Calcd. for $C_{46}H_{52}N_4O_{12}$ (852.91): C, 64.77; H, 6.15; N, 6.57. Found: C, 64.66; H, 6.46; N, 6.54, benzyl (benzyl 2-acetamido-4,6-O-benzylidene-2-deoxy-α-D-glucopyranosid-3-O-yl)-acetyl-O-benzyl-L-threonine-D-isoglutaminate, benzyl (benzyl 2-acetamido-4,6-O-benzylidene-2-deoxy-α-D-glucopyranosid-3-O-yl)-acetyl-L-methionyl-D-isoglutaminate having a melting point of 234°–238° C; $[\alpha]_D^{25} + 78.0°$ (10 mg/ml, dimethylformamide);

Anal. Calcd. for $C_{41}H_{50}N_4O_{11}S$ (806.95): C, 61.03; H, 6.25; N, 6.94. Found: C, 60.98; H, 6.38; N, 6.86, benzyl (benzyl 2-acetamido-4,6-O-benzylidene-2-deoxy-α-D-glucopyranosid-3-O-yl)-acetyl-S-benzyl-L-cysteinyl-D-isoglutaminate, benzyl (benzyl 2-acetamido-4,6-O-benzylidene-2-deoxy-α-D-glucopyranosid-3-O-yl)-acetyl-L-phenylalanyl-D-isoglutaminate, having a melting point of 229°–231° C;

Anal. Calcd. for $C_{45}H_{50}N_4O_{11}$ (822.93): C, 65.68; H, 6.12; N, 6.81 Found: C, 65.63 H, 6.02, N, 6.62, benzyl (benzyl 2-acetamido-4,6-O-benzylidene-2-deoxy-α-D-glucopyranosid-3-O-yl)-acetyl-O-benzyl-L-tyrosyl-D-isoglutaminate having a melting point of 241°–243° C; $[\alpha]_D^{23} + 66.7°$ (4.2 mg/ml, dimethylformamide);

benzyl (benzyl 2-acetamido-4,6-O-benzylidene-2-deoxy-α-D-glucopyranosid-3-O-yl)-acetyl-L-tryptophanol-D-isoglutaminate, benzyl (benzyl 2-acetamido-4,6-O-benzylidene-2-deoxy-α-D-glucopyranosid-3-O-yl)-acetyl-ε-carbobenzyloxy-L-lysyl-D-isoglutaminate having a melting point of 215°–219° C; $[\alpha]_D^{25} + 66.7°$ (5.5 mg/ml, dimethylformamide);

Anal. Calcd. for $C_{50}H_{59}N_5O_{13}$ (938.06): C, 64.02; H, 6.34; N, 7.47. Found: C, 63.79; H; 6.51; N, 7.44, benzyl (benzyl 2-acetamido-4,6-O-benzylidene-2-deoxy-α-D-glucopyranosid-3-O-yl)-acetyl-δ-carbobenzyloxy-L-ornithyl-D-isoglutaminate, benzyl (benzyl 2-acetamido-4,6-O-benzylidene-2-deoxy-α-D-glucopyranosid-3-O-yl)-acetyl-gu-nitro-L-arginyl-D-isoglutaminate, benzyl (benzyl 2-acetamido-4,6-O-benzylidene-2-deoxy-α-D-glucopyranosid-3-O-yl)-acetyl-$N^{Im}$-benzyl-L-histidyl-D-isoglutaminate, benzyl (benzyl 2-acetamido-4,6-O-benzylidene-2-deoxy-α-D-glucopyranosid-3-O-yl)-acetyl-γ-benzyl-L-glutamyl-D-isoglutaminate, benzyl (benzyl 2-acetamido-4,6-O-benzylidene-2-deoxy-α-D-glucopyranosid-3-O-yl)-acetyl-L-glutaminyl-D-isoglutaminate, benzyl (benzyl 2-acetamido-4,6-O-benzylidene-2-deoxy-α-D-glucopyranosid-3-O-yl)-acetyl-β-benzyl-L-aspartyl-D-isoglutaminate, benzyl (benzyl 2-acetamido-4,6-O-benzylidene-2-deoxy-α-D-glucopyranosid-3-O-yl)-acetyl-L-asparginyl-D-isoglutaminate, benzyl (benzyl 2-acetamido-4,6-O-benzylidene-2-deoxy-α-D-glucopyranosid-3-O-yl)-acetyl-L-prolyl-D-isoglutaminate having a melting point of 224°–225° C; $[\alpha]_D^{24} + 68.1°$ (3.1 mg/ml, dimethylformamide);

Anal. Calcd. for $C_{41}H_{48}N_4O_{11}$ (772.82): C, 63.72; H, 6.26; N, 7.25. Found: C, 63.49; H, 6.39; N, 7.14, benzyl (benzyl 2-acetamido-4,6-O-benzylidene-2-deoxy-α-D-glucopyranosid-3-O-yl)-acetyl-O-benzyl-L-hydroxyprolyl-D-isoglutaminate, benzyl (benzyl 2-acetamido-4,6-O-benzylidene-2-deoxy-α-D-glucopyranosid-3-O-yl)-acetyl-L-alanyl-D-isoasparaginate having a melting point of 222°–225° C; $[\alpha]_D^{25} + 97.1°$ (10 mg/ml, dimethylformamide);

Anal. Calcd. for $C_{38}H_{44}N_4O_{11}$ (732.80): C, 62.28; H, 6.05; N, 7.65. Found: C, 62.48; H, 6.18; N, 7.60, benzyl (benzyl 2-acetamido-4,6-O-benzylidene-2-deoxy-α-D-glucopyranosid-3-O-yl)acetyl-L-valyl-D-isoasparaginate, benzyl (benzyl 2-acetamido-4,6-O-benzylidene-2-deoxy-α-D-glucopyranosid-3-O-yl)-acetyl-L-leucyl-D-isoasparaginate, benzyl (benzyl 2-acetamido-4,6-O-benzylidene-2-deoxy-α-D-glucopyranosid-3-O-yl)-acetyl-L-isoleucyl-D-isoasparaginate, benzyl (benzyl 2-acetamido-4,6-O-benzylidene-2-deoxy-α-D-glucopyranosid-3-O-yl)-acetyl-L-α-aminobutyryl-D-isoasparaginate, benzyl (benzyl 2-acetamido-4,6-O-benzylidene-2-deoxy-α-D-glucopyranosid-3-O-yl)-acetyl-O-benzyl-L-seryl-D-isoasparaginate, benzyl (benzyl 2-acetamido-4,6-O-benzylidene-2-deoxy-α-D-glucopyranosid-3-O-yl)-acetyl-O-benzyl-L-threonyl-D-isoasparaginate, benzyl (benzyl 2-acetamido-4,6-O-benzylidene-2-deoxy-α-D-glucopyranosid-3-O-yl)-acetyl-L-methionyl-D-isoasparaginate, benzyl (benzyl 2-acetamido-4,6-O-benzylidene-2-deoxy-α-D-glucopyranosid-3-O-yl)-acetyl-S-benzyl-L-cysteinyl-D-isoasparaginate, benzyl (benzyl 2-acetamido-4,6-O-benzylidene-2-deoxy-α-D-glucopyranosid-3-O-yl)-acetyl-L-phenylalanyl-D-isoasparaginate, benzyl (benzyl 2-acetamido-4,6-O-benzylidene-2-deoxy-α-D-glucopyranosid-3-O-yl)-acetyl-O-benzyl-L-tyrosinyl-D-isoasparaginate, benzyl (benzyl 2-acetamido-4,6-O-benzylidene-2-deoxy-α-D-glucopyranosid-3-O-yl)-acetyl-L-tryptophanyl-D-isoasparaginate, benzyl (benzyl 2-acetamido-4,6-O-benzylidene-2-deoxy-α-D-glucopyranosid-3-O-yl)-acetyl-ε-carbobenzyloxy-L-lysyl-D-isoasparaginate, benzyl (benzyl 2-acetamido-4-6,-O-benzylidene-2-deoxy-α-D-glucopyranosid-3-O-yl)-acetyl-δ-carbobenzyloxy-L-ornithyl-D-isoasparaginate, benzyl (benzyl 2-acetamido-4,6-O-benzylidene-2-deoxy-α-D-glucopyranosid-3-O-yl)-acetyl-gu-nitro-L-arginyl-D-isoasparaginate, benzyl (benzyl 2-acetamido-4,6-O-benzylidene-2-deoxy-α-D-glucopyranosid-3-O-yl)-acetyl-N$^{Im}$-benzyl-L- histidyl-D-isoasparaginate, benzyl (benzyl 2-acetamido-4,6-O-benzylidene-2-deoxy-α-D-glucopyranosid-3-O-yl)-acetyl-γ-benzyl-L-glutamyl-D-isoasparaginate, benzyl (benzyl 2-acetamido-4,6-O-benzylidene-2-deoxy-α-D-glucopyranosid-3-O-yl)-acetyl-L-glutaminyl-D-isoasparaginate, benzyl (benzyl 2-acetamido-4,6-O-benzylidene-2-deoxy-α-D-glucopyranosid-3-O-yl)-acetyl-β-benzyl-L-aspartyl-D-isoasparaginate, benzyl (benzyl 2-acetamido-4,6-O-benzylidene-2-deoxy-α-D-glucopyranosid-3-O-yl)acetyl-L-asparaginyl-D-isoasparaginate, benzyl (benzyl 2-acetamido-4,6-O-benzylidene-2-deoxy-α-D-glucopyranosid-3-O-yl)-acetyl-L-prolyl-D-isoasparaginate, and benzyl (benzyl 2-acetamido-4,6-O-benzylidene-2-deoxy-α-D-glucopyranosid-3-O-yl)-acetyl-O-benzyl-L-hydroxyprolyl-D-isoasparaginate.

In like manner by substituting a stoichiometric equivalent amount of the compounds obtained in Example 6 for benzyl 2-acetamido-4,6-O-benzylidene 2-deoxy-3-O-carboxymethyl-α-D-glucopyranoside and reacting them with each of the appropriate compounds obtained in Example 4 there are obtained the various corresponding compounds of Formula (11).

EXAMPLE 8

300 Ml of 67% acetic acid is heated to 97° C on a steam bath and 3.71 g of benzyl (benzyl 2-acetamido-4,6-O-benzylidene-2-deoxy-α-D-glucopyranoside-3-O-yl)acetyl-L-alanyl-D-isoglutaminate (11, $n$ = 2, $X^1$ = L-alanyl, $R^2$ = $CH_3$) is added. The resulting solution is heated at 97°–100° C for exactly 7 minutes and then immediately chilled in an ice bath. The solution is evaporated to dryness in vacuo and the residue is freed of acetic acid by two co-evaporations with water and two co-evaporations with toluene giving 3.5 g of crude product to which 250 ml of ether is added and the residue is magnetically stirred at 22° C for 15 hours. The resultant solid is collected by filtration and dried giving 3.18 g of benzyl (benzyl 2-acetamido-2-deoxy-α-D-glucopyranosid-3-O-yl)acetyl-L-alanyl-D-isoglutaminate (12A, $n$ = 2, $X^1$ = L-alanyl, $R^2$ = $CH_3$) having a melting point of 202° – 203° C; $[α]_D^{25}$ + 65.8° (2.3mg/ml, methanol);

Anal: Calcd. for $C_{32}H_{42}N_4O_{11}$ (658.72): C, 58.35; H, 6.43; N, 8.51. Found: C, 58.28; H, 6.13; N, 8.54

In like manner substituting a stoichiometric equivalent amount of the compounds obtained in Example 7 for benzyl (benzyl 2-acetamido-4,6-O-benzylidene-2-deoxy-α-D-glucopyranoisid-3-O-yl) acetyl-L-alanyl-D-isoglutaminate there are obtained the corresponding compounds of Formula (12A).

EXAMPLE 9

A solution of 0.66 g of benzyl (benzyl 2-acetamido-2-deoxy-α-D-glucopyranosid-3-O-yl)acetyl-L-alanyl-D-isoglutaminate (12A, $n$ = 2, $X^1$ = L-alanyl, $R^2$ = $CH_3$) and 0.56 g of triphenylmethyl chloride in 10 ml of pyridine is stirred at 22° C for 5 days and is then evaporated to dryness in vacuo. The residue is partitioned between 30 ml of chloroform and 30 ml of water, the chloroform phase is extracted twice more with 30 ml of water, dried over magnesium sulfate, concentrated in vacuo and the residue is triturated with 50 ml of ether. The resulting solid is collected by filtration, washed with ether and dried giving 0.74 g of benzyl (benzyl 2-acetamido-2-deoxy-6-O-triphenylmethyl-α-D-glucopyranosid-3-O-yl)acetyl-L-alanyl-D-isoglutaminate (12B, $n$ = 2, $X^1$ = L-alanyl, $R^2$ = $CH_3$).

In like manner by substituting a stoichiometric equivalent amount of the compounds obtained in Example 8 for benzyl (benzyl 2-acetamido-2-deoxy-α-D-glucopyranosid-3-O-yl)acetyl-alanyl-D-isoglutaminate there are obtained the compounds of Formula (12B).

EXAMPLE 10

A solution of 0.33 g of benzyl (benzyl 2-acetamido-2-deoxy-α-D-glucopyranosid-3-O-yl) acetyl-L-alanyl-D-isoglutaminate (12A, $n$ = 2, $X^1$ = L-alanyl, $R^2$ = $CH_3$) and 1.0 ml of acetic anhydride in 5 ml of pyridine is stored at 22° C for 16 hours at which time 1 ml of methanol is added and the resulting solution is stirred at room temperature for a further 1 hour. The solution is then evaporated to dryness, the residue is partitioned between 20 ml of chloroform and 20 ml of water and the chloroform phase is dried over magnesium sulfate and evaporated to dryness giving 0.38 g of crude product which is crystallized from aqueous ethanol giving 0.34 g of benzyl (benzyl 2-acetamido-4,6-di-O-acetyl-2-deoxy-α-D-glucopyranosid-3-O-yl)acetyl-L-alanyl-D-isoglutaminate (12E, $n$ = 2, $X^1$ = L-alanyl, $R^2$ = $CH_3$, $R^4$ = $R^5$ = $COCH_3$) having a melting point of 185°–6° C; $[α]_D^{25}$ + 64.8° (3 mg/ml, methanol):

Anal. Calcd for $C_{36}H_{46}N_4O_{13}$ (742.80): C, 58.21; H, 6.24; N, 7.54 Found: C, 58.47; H, 6.01; N, 7.52.

In like manner substituting a stoichiometric equivalent amount of the appropriate acylating agent (either acid anhydride or acid chloride) for acetic anhydride there are obtained the corresponding compounds of Formula (12E).

In like manner substituting a stoichiometric equivalent amount of the compounds obtained in Example 8 for benzyl (benzyl 2-acetamido-2-deoxy-α-D-glucopyranosid-3-O-yl)acetyl-L-alanyl-D-isoglutaminate there are obtained the corresponding compounds of Formula (12E).

EXAMPLE 11

By repeating the procedure of Example 10 but replacing benzyl (benzyl 2-acetamido-2-deoxy-α-D- glucopyranosid-3-O-yl) acetyl-L-alanyl-D-isoglutaminate with a stoichiometric equivalent amount of benzyl (benzyl 2-acetamido-2-deoxy-6-O-triphenylmethyl-α-D-glucopyranosid-3-O-yl)acetyl-L-alanyl-D-isoglutaminate (12B, $n = 2$, $X^1$ = L-alanyl, $R^2$ = $CH_3$) there is obtained benzyl (benzyl 2-acetamido-4-O-acetyl-2-deoxy-6-O-triphenylmethyl-α-D-glucopyranosid-3-O-yl) acetyl-L-alanyl-D-isoglutaminate (12C, $n = 2$, $X^1$ = L-alanyl, $R^2$ = $CH_3$, $R^3$ = $COCH_3$).

In like manner substituting a stoichiometric equivalent amount of the appropriate acylating agent (either acid anhydride or acid chloride) for acetic anhydride there are obtained the corresponding compounds of Formula (12E).

EXAMPLE 12

A mixture of 0.94 g of benzyl (benzyl 2-acetamido-4-O-acetyl-6-O-triphenylmethyl-α-D-glucopyranosid-3-O-yl)acetyl-L-alanyl-D-isoglutaminate (12C, $n = 2$, $X^1$ = L-alanyl, $R^2$ = $CH_3$, $R^3$ = —$COCH_3$) and 10 ml of 70% acetic acid is heated at a 100° C until a clear solution is obtained (about 2 minutes) and heating is contained for a further 2 minutes. The solution is immediately cooled in an ice bath and the precipitate is removed by filtration. The filtrate is evaporated to dryness in vacuo, the residue is triturated with 25 ml ether and the resultant solid is collected by filtration, washed with ether and dried in vacuo giving benzyl (benzyl 2-acetamido-4-O-acetyl-α-D-glucopyranosid-3-O-yl)acetyl-L-alanyl-D-isoglutaminate (12C, $n = 2$, $X^1$ = L-alanyl, $R^2$ = $CH_3$, $R^3$ = $COCH_3$).

In like manner substituting a stoichiometric equivalent amount of the compounds obtained in Example 11 for benzyl (benzyl 2-acetamido-4-O-acetyl-6-O-triphenylmethyl-α-D-glucopyranosid-3-O-yl)acetyl-L-alanyl-D-isoglutaminate there are obtained the corresponding compounds of Formula (12D).

EXAMPLE 13

By repeating the procedure of Example 10 but replacing benzyl (benzyl 2-acetamido-2-deoxy-α-D-glucopyranosid-3-O-yl) acetyl-L-alanyl-D-isoglutaminate with a stoichiometric equivalent amount of benzyl (benzyl 2-acetamido-4-O-acetyl-α-D-glucopyranosid-3-O-yl)acetyl-L-alanyl-D-isoglutaminate (12D, $n = 2$, $X^1$ = L-alanyl, $R^2$ = $CH_3$, $R^3$ = —$COCH_3$) and using propionic anhydride instead of acetic anhydride there is obtained benzyl (benzyl 2-acetamido-4-O-acetyl-6-O-propionyl-α-D-glucopyranosid-3-O-yl) acetyl-L-alanyl-D-isoglutaminate (12E, $n = 2$, $X^1$ = L-alanyl, $R^2$ = $CH_3$, $R^5$ = —$COCH_3$, $R^4$ = —$COC_2H_5$).

In like manner substituting a stoichiometric equivalent amount of the appropriate acylating agent (acid anhydride or acid chloride) for propionic anhydride there are obtained the corresponding compounds of Formula (12E).

In like manner substituting a stoichiometric equivalent amount of the compounds obtained in Example 12 for benzyl (benzyl 2-acetamido-4-O-acetyl-α-D-glucopyranosid-3-O-yl)-acetyl-L-alanyl-D-isoglutaminate there are obtained the corresponding compounds of Formula (12E).

EXAMPLE 14

A solution of 0.33 g of benzyl (benzyl 2-acetamido-2-deoxy-α-D-glucopyranosid-3-O-yl)acetyl-L-alanyl-D-isoglutaminate (12A, $n = 2$, $X^1$ = L-alanyl, $R^2$ = $CH_3$) in 5 ml of pyridine is stirred at 0° whilst a solution of 0.095 ml of acetic anhydride in 1 ml of pyridine is added dropwise over 30 minutes. The resultant solution is stored at 0° C for 16 hours at which time 1 ml of methanol is added and the mixture is evaporated to dryness. The residue thus obtained is partitioned between 100 ml of chloroform and 100 ml of water, the chloroform phase is dried over magnesium sulfate and concentrated in vacuo, giving 0.36 g of crude product which is purified by preparative thick-layer chromatography giving benzyl (benzyl 2-acetamido-6-O-acetyl-2-deoxy-α-D-glucopyranosid-3-O-yl)acetyl-L-alanyl-D-isoglutamine (12F, $n = 2$, $X^1$=L-alanyl, $R^2$ = $CH_3$, $R^3$ = —$COCH_3$).

In like manner by substituting a stoichiometric equivalent amount of the appropriate acylating agent (either acid anhydride or acid chloride) for acetic anhydride there are obtained the corresponding compounds of Formula (12F).

In like manner substituting a stoichiometric equivalent amount of the compounds obtained in Example 8 for benzyl (benzyl 2-acetamido-2-deoxy-α-D-glucopyranosid-3-O-yl)acetyl-L-alanyl-D-isoglutaminate there are obtained the compounds of Formula (12F).

EXAMPLE 15

A mixture of 0.205 g of benzyl (benzyl 2-acetamido-4,6-O-benzylidene-2-deoxy-α-D-glucopyranosid-3-O-yl)-acetyl-L-alanyl-D-isoglutaminate (11, $n = 2$, $X^1$ = L-alanyl, $R^2$ = $CH_3$) and 50 mg of a 10% palladium on carbon catalyst in 15 ml of 85% acetic acid is magnetically stirred at 22° C in a hydrogen atmosphere. The formation of the product (13, $n = 2$, X = L-alanyl, $R^2$ = $CH_3$) is monitored by thin layer chromatography using the solvent system comprising acetonitrile:acetic acid:water in a ratio of 8:1:1. The reaction is generally found to be complete within a 24-40 hour period whence the catalyst is removed by filtration through a millipore filter (teflon) and the filtrate is evaporated to dryness in vacuo to give a residue which is dissolved in 3 ml of methanol and the product is precipitated by the addition of 8 ml of ethyl acetate. The thus obtained white solid is collected by centrifugation and dried carefully in vacuo to give 52 mg of a white powder which is dissolved in 5 ml of water, and this solution is then loaded onto a 20 cm × 0.5 cm column of BI-OREX ®70 (weakly acidic ion-exchange resin of polyacrylic acid). The column is eluted with water and the fractions containing the required product are pooled and lyophilised to give 33 mg of 2-acetamido-2-deoxy-D-glucos-3-O-yl-acetyl-L-alanyl-D-isoglutamine (13, $n = 2$, X = L-alanyl, R = $R^1$ = hydrogen, $R^2$ = $CH_3$) having a melting point of 148° C (decomposition); $[\alpha]_D^{24}$ + 18.6° (5.0 mg/ml, methanol).

In like manner substituting a stoichiometric equivalent amount of the various products from Example 7, for benzyl (benzyl 2-acetamido-4,6-O-benzylidene-2-deoxy-α-D-glucopyranosid-3-O-yl)acetyl-L-alanyl-D-isoglutaminate there are obtained the corresponding glycopeptides. Representative compounds thus obtained are:

2-acetamido-2-deoxy-D-glucos-3-O-yl-acetyl-L-valyl-D-isoglutamine having a melting point of 140°–150° C (decomposition); $[\alpha]_D^{25}$ + 13.6° (10 mg/ml, methanol), 2-acetamido-2-deoxy-D-glucos-3-O-yl-acetyl-L-leucyl-D-isoglutamine, having a melting point of 133°–135° C, 2-acetamido-2-deoxy-D-glucos-3-O-yl-acetyl-L-isoleucyl-D-isoglutamine, 2-acetamido-2-deoxy-D-glucos-3-O-yl-acetyl-L-α-aminobutyryl-D-isoglutamine, 2-acetamido-2-deoxy-D-glucos-3-O-yl-acetyl-L-seryl-D-isoglutamine having a melting point of 132° (decomposition); $[\alpha]_D^{23} + 19.4°$ (5.6 mg/ml, methanol), 2-acetamido-2-deoxy-D-glucos-3-O-yl-acetyl-L-threonyl-D-isoglutamine, 2-acetamido-2-deoxy-D-glucos-3-O-yl-acetyl-L-methionyl-D-isoglutamine, 2-acetamido-2-deoxy-D-glucos-3-O-yl-acetyl-L-cysteinyl-D-isoglutamine, 2-acetamido-2-deoxy-D-glucos-3-O-yl-acetyl-L-phenylalanyl-D-isoglutamine, having a melting point of 136°–140° C, 2-acetamido-2-deoxy-D-glucos-3-O-yl-acetyl-L-tyrosyl-D-isoglutamine, having a melting point of 153° C (decomposition); $[\alpha]_D^{25} + 37.7°$ (5.0 mg/ml, methanol), 2-acetamido-2-deoxy-D-glucos-3-O-yl-acetyl-L-tryptophanyl-D-isoglutamine, 2-acetamido-2-deoxy-D-glucos-3-O-yl-acetyl-L-lysyl-D-isoglutamine, having a melting point of 126°–133° C (decomposition); $[\alpha]_D^{25} + 10.0°$ (5 mg/ml, methanol), 2-acetamido-2-deoxy-D-glucos-3-O-yl-acetyl-L-ornithyl-D-isoglutamine, 2-acetamido-2-deoxy-D-glucos-3-O-yl-acetyl-L-arginyl-D-isoglutamine, 2-acetamido-2-deoxy-D-glucos-3-O-yl-acetyl-L-histidyl-D-isoglutamine, 2-acetamido-2-deoxy-D-glucos-3-O-yl-acetyl-L-glutamyl-D-isoglutamine, 2-acetamido-2-deoxy-D-glucos-3-O-yl-acetyl-L-glutaminyl-D-isoglutamine, 2-acetamido-2-deoxy-D-glucos-3-O-yl-acetyl-L-aspartyl-D-isoglutamine, 2-acetamido-2-deoxy-D-glucos-3-O-yl-acetyl-L-asparaginyl-D-isoglutamine, 2-acetamido-2-deoxy-D-glucos-3-O-yl-acetyl-L-prolyl-D-isoglutamine having a melting point of 144°–146° C; $[\alpha]_D^{23} - 10.5°$ (5.9 mg/ml, methanol), 2-acetamido-2-deoxy-D-glucos-3-O-yl-acetyl-L-hydroxyprolyl-D-isoglutamine, 2-acetamido-2-deoxy-D-glucos-3-O-yl-acetyl-L-alanyl-D-isoasparagine having a melting point of 140°–145° C (decomposition); $[\alpha]_D^{24} + 18.4°$ (10.0 mg/ml, methanol), 2-acetamido-2-deoxy-D-glucos-3-O-yl-acetyl-L-valyl-D-isoasparagine, 2-acetamido-2-deoxy-D-glucos-3-O-yl-acetyl-L-leucyl-D-isoasparagine, 2-acetamido-2-deoxy-D-glucos-3-O-yl-acetyl-L-isoleucyl-D-isoasparagine, 2-acetamido-2-deoxy-D-glucos-3-O-yl-acetyl-L-α-amino-butyryl-D-isoasparagine, 2-acetamido-2-deoxy-D-glucos-3-O-yl-acetyl-L-seryl-D-isoasparagine, 2-acetamido-2-deoxy-D-glucos-3-O-yl-acetyl-L-threonyl-D-isoasparagine, 2-acetamido-2-deoxy-D-glucos-3-O-yl-acetyl-L-methionyl-D-isoasparagine, 2-acetamido-2-deoxy-D-glucos-3-O-yl-acetyl-L-cysteinyl-D-isoasparagine, 2-acetamido-2-deoxy-D-glucos-3-O-yl-acetyl-L-phenyl-alanyl-D-isoasparagine, 2-acetamido-2-deoxy-D-glucos-3-O-yl-acetyl-L-tyrosyl-D-isoasparagine, 2-acetamido-2-deoxy-D-glucos-3-O-yl-acetyl-L-tryptophanyl-D-isoasparagine, 2-acetamido-2-deoxy-D-glucos-3-O-yl-acetyl-L-lysyl-D-isoasparagine, 2-acetamido-2-deoxy-D-glucos-3-O-yl-acetyl-L-ornithyl-D-isoasparagine, 2-acetamido-2-deoxy-D-glucos-3-O-yl-acetyl-L-arginyl-D-isoasparagine, 2-acetamido-2-deoxy-D-glucos-3-O-yl-acetyl-L-histidyl-D-isoasparagine, 2-acetamido-2-deoxy-D-glucos-3-O-yl-acetyl-L-glutamyl-D-isoasparagine, 2-acetamido-2-deoxy-D-glucos-3-O-yl-acetyl-L-glutaminyl-D-isoasparagine, 2-acetamido-2-deoxy-D-glucos-3-O-yl-acetyl-L-aspartyl-D-isoasparagine, 2-acetamido-2-deoxy-D-glucos-3-O-yl-acetyl-L-asparaginyl-D-isoasparagine, 2-acetamido-2-deoxy-D-glucos-3-O-yl-acetyl-L-prolyl-D-isoasparagine, 2-acetamido-2-deoxy-D-glucos-3-O-yl-acetyl-L-hydroxyprolyl-D-isoasparagine, 2-glycolamido-2-deoxy-D-glucos-3-O-yl-acetyl-L-alanyl-D-isoglutamine, 2-glycolamido-2-deoxy-D-glucos-3-O-yl-acetyl-L-valyl-D-isoglutamine, 2-glycolamido-2-deoxy-D-glucos-3-O-yl-acetyl-L-leucyl-D-isoglutamine, 2-glycolamido-2-deoxy-D-glucos-3-O-yl-acetyl-L-isoleucyl-D-isoglutamine, 2-glycolamido-2-deoxy-D-glucos-3-O-yl-acetyl-L-seryl-D-isoglutamine, 2-glycolamido-2-deoxy-D-glucos-3-O-yl-acetyl-L-threonyl-D-isoglutamine, 2-glycolamido-2-deoxy-D-glucos-3-O-yl-acetyl-L-methionyl-D-isoglutamine, 2-glycolamido-2-deoxy-D-glucos-3-O-yl-acetyl-L-cysteinyl-D-isoglutamine, 2-glycolamido-2-deoxy-D-glucos-3-O-yl-acetyl-L-acetyl-phenylalanyl-D-isoglutamine, 2-glycolamido-2-deoxy-D-glucos-3-O-yl-acetyl-L-tyrosyl-D-isoglutamine, 2-glycolamido-2-deoxy-D-glucos-3-O-yl-acetyl-L-tryptophanyl-D-isoglutamine, 2-glycolamido-2-deoxy-D-glucos-3-O-yl-acetyl-L-histidyl-D-isoglutamine, 2-glycolamido-2-deoxy-D-glucos-3-O-yl-acetyl-L-glutamyl-D-isoglutamine, 2-glycolamido-2-deoxy-D-glucos-3-O-yl-acetyl-L-glutaminyl-D-isoglutamine, 2-glycolamido-2-deoxy-D-glucos-3-O-yl-acetyl-L-aspartyl-D-isoglutamine, 2-glycolamido-2-deoxy-D-glucos-3-O-yl-acetyl-L-asparaginyl-D-isoglutamine, 2-glycolamido-2-deoxy-D-glucos-3-O-yl-acetyl-L-prolyl-D-isoglutamine, 2-glycolamido-2-deoxy-D-glucos-3-acetyl-L-hydroxyprolyl-D-isoglutamine, 2-glycolamido-2-deoxy-D-glucos-3-O-yl-acetyl-L-alanyl-D-isoasparagine, 2-benzamido-2-deoxy-D-glucos-3-O-yl-acetyl-L-alanyl-D-isoglutamine, 2-benzamido-2-deoxy-D-glucos-3-O-yl-acetyl-L-valyl-D-isoglutamine, 2-benzamido-2-deoxy-D-glucos-3-O-yl-acetyl-L-prolyl-D-isoglutamine, 2-benzamido-2-deoxy-D-glucos-3-O-yl-acetyl-L-seryl-D-isoglutamine,
2-benzamido-2-deoxy-D-glucos-3-O-yl-acetyl-L-phenylalanyl-D-isoglutamine,
2-trifluoroacetamido-2-deoxy-D-glucos-3-O-yl-acetyl-L-alanyl-D-isoglutamine,
2-trifluoroacetamido-2-deoxy-D-glucos-3-O-yl-acetyl-L-valyl-D-isoglutamine,
2-trifluoroacetamido-2-deoxy-D-glucos-3-O-yl-acetyl-L-prolyl-D-isoglutamine,
2-trifluoroacetamido-2-deoxy-D-glucos-3-O-yl-acetyl-L-seryl-D-isoglutamine,
2-trifluoroacetamido-2-deoxy-D-glucos-3-O-yl-acetyl-L-phenylalanyl-D-isoglutamine,
2-methoxyacetamido-2-deoxy-D-glucos-3-O-yl-acetyl-L-alanyl-D-isoglutamine,
2-methoxyacetamido-2-deoxy-D-glucos-3-O-yl-acetyl-L-valyl-D-isoglutamine,
2-methoxyacetamido-2-deoxy-D-glucos-3-O-yl-acetyl-L-prolyl-D-isoglutamine,
2-methoxyacetamido-2-deoxy-D-glucos-3-O-yl-acetyl-L-seryl-D-isoglutamine,
2-methoxyacetamido-2-deoxy-D-glucos-3-O-yl-acetyl-L-phenylalanyl-D-isoglutamine,
2-myristamido-2-deoxy-D-glucos-3-O-yl-acetyl-L-alanyl-D-isoglutamine,
2-myristamido-2-deoxy-D-glucos-3-O-yl-acetyl-L-valyl-D-isoglutamine,
2-myristamido-2-deoxy-D-glucos-3-O-yl-acetyl-L-prolyl-D-isoglutamine,
2-myristamido-2-deoxy-D-glucos-3-O-yl-acetyl-L-seryl-D-isoglutamine, and
2-myristamido-2-deoxy-D-glucos-3-O-yl-acetyl-L-phenylalanyl-D-isoglutamine.

In like manner substituting a stoichiometric equivalent amount of the various products from Example 10 for benzyl (benzyl 2-acetamido-4,6-O-benzylidene-2-deoxy-α-D-glucopyranosid-3-O-yl) acetyl-L-alanyl-D-isoglutaminate there are obtained the corresponding compounds of Formula (13). Representative compounds thus obtained are:

4,6-di-O-acetyl-2-acetamido-2-deoxy-D-glucos-3-O-yl-acetyl-L-alanyl-D-isoglutamine having a melting point of 140°-160° C,
4,6-di-O-acetyl-2-acetamido-2-deoxy-D-glucos-3-O-yl-acetyl-L-valyl-D-isoglutamine,
4,6-di-O-acetyl-2-acetamido-2-deoxy-D-glucos-3-O-yl-acetyl-L-prolyl-D-isoglutamine,
4,6-di-O-acetyl-2-acetamido-2-deoxy-D-glucos-3-O-yl-acetyl-L-seryl-D-isoglutamine,
4,6-di-O-acetyl-2-acetamido-2-deoxy-D-glucos-3-O-yl-acetyl-L-phenylalanyl-D-isoglutamine,
4,6-di-O-acetyl-2-glycolamido-2-deoxy-D-glucos-3-O-yl-acetyl-L-alanyl-D-isoglutamine,
4,6-di-O-acetyl-2-glycolamido-2-deoxy-D-glucos-3-O-yl-acetyl-L-valyl-D-isoglutamine,
4,6-di-O-acetyl-2-glycolamido-2-deoxy-D-glucos-3-O-yl-acetyl-L-prolyl-D-isoglutamine,
4,6-di-O-acetyl-2-glycolamido-2-deoxy-D-glucos-3-O-yl-acetyl-L-seryl-D-isoglutamine,
4,6-di-O-acetyl-2-glycolamido-2-deoxy-D-glucos-3-O-yl-acetyl-L-phenylalanyl-D-isoglutamine,
4,6-di-O-acetyl-2-benzamido-2-deoxy-D-glucos-3-O-yl-acetyl-L-alanyl-D-isoglutamine,
4,6-di-O-acetyl-2-trifluoroacetamido-2-deoxy-D-glucos-3-O-yl-acetyl-L-alanyl-D-isoglutamine,
4,6-di-O-acetyl-2-methoxyacetamido-2-deoxy-D-glucos-3-O-yl-acetyl-L-alanyl-D-isoglutamine,
4,6-di-O-acetyl-2-myristamido-2-deoxy-D-glucos-3-O-yl-acetyl-L-alanyl-D-isoglutamine,
4,6-di-O-butyryl-2-acetamido-2-deoxy-D-glucos-3-O-yl-acetyl-L-alanyl-D-isoglutamine,
4,6-di-O-butyryl-2-acetamido-2-deoxy-D-glucos-3-O-yl-acetyl-L-valyl-D-isoglutamine,
4,6-di-O-butyryl-2-acetamido-2-deoxy-D-glucos-3-O-yl-acetyl-L-prolyl-D-isoglutamine,
4,6-di-O-butyryl-2-acetamido-2-deoxy-D-glucos-3-O-yl-acetyl-L-seryl-D-isoglutamine,
4,6-di-O-butyryl-2-acetamido-2-deoxy-D-glucos-3-O-yl-acetyl-L-phenylalanyl-D-isoglutamine,
4,6-di-O-butyryl-2-glycolamido-2-deoxy-D-glucos-3-O-yl-acetyl-L-alanyl-D-isoglutamine,
4,6-di-O-butyryl-2-glycolamido-2-deoxy-D-glucos-3-O-yl-acetyl-L-valyl-D-isoglutamine,
4,6-di-O-butyryl-2-glycolamido-2-deoxy-D-glucos-3-O-yl-acetyl-L-prolyl-D-isoglutamine,
4,6-di-O-butyryl-2-glycolamido-2-deoxy-D-glucos-3-O-yl-acetyl-L-seryl-D-isoglutamine,
4,6-di-O-butyryl-2-glycolamido-2-deoxy-D-glucos-3-O-yl-acetyl-L-phenylalanyl-D-isoglutamine,
4,6-di-O-butyryl-2-benzamido-2-deoxy-D-glucos-3-O-yl-acetyl-L-alanyl-D-isoglutamine,
4,6-di-O-butyryl-2-trifluoroacetamido-2-deoxy-D-glucos-3-O-yl-acetyl-L-alanyl-D-isoglutamine,
4,6-di-O-butyryl-2-methoxyacetamido-2-deoxy-D-glucos-3-O-yl-acetyl-L-alanyl-D-isoglutamine, and
4,6-di-O-butyryl-2-myristamido-2-deoxy-D-glucos-3-O-yl-acetyl-L-alanyl-D-isoglutamine.
4,6-di-O-octanoyl-2-acetamido-2-deoxy-D-glucos-3-O-yl-acetyl-L-alanyl-D-isoglutamine,
4,6-di-O-octanoyl-2-acetamido-2-deoxy-D-glucos-3-O-yl-acetyl-L-valyl-D-isoglutamine,
4,6-di-O-octanoyl-2-acetamido-2-deoxy-D-glucos-3-O-yl-acetyl-L-prolyl-D-isoglutamine,
4,6-di-O-octanoyl-2-acetamido-2-deoxy-D-glucos-3-O-yl-acetyl-L-seryl-D-isoglutamine,
4,6-di-O-octanoyl-2-acetamido-2-deoxy-D-glucos-3-O-yl-acetyl-L-phenylalanyl-D-isoglutamine,
4,6-di-O-octanoyl-2-glycolamido-2-deoxy-D-glucos-3-O-yl-acetyl-L-alanyl-D-isoglutamine,
4,6-di-O-octanoyl-2-glycolamido-2-deoxy-D-glucos-3-Oyl-acetyl-L-valyl-D-isoglutamine,
4,6-di-O-octanoyl-2-glycolamido-2-deoxy-D-glucos-3-O-yl-acetyl-L-prolyl-D-isoglutamine,
4,6-di-O-octanoyl-2-glycolamido-2-deoxy-D-glucos-3-O-yl-acetyl-L-seryl-D-isoglutamine,
4,6-di-O-octanoyl-2-glycolamido-2-deoxy-D-glucos-3-O-yl-acetyl-L-phenylalanyl-D-isoglutamine,
4,6-di-O-octanoyl-2-benzamido-2-deoxy-D-glucos-3-O-yl-acetyl-L-alanyl-D-isoglutamine,
4,6-di-O-octanoyl-2-trifluoroacetamido-2-deoxy-D-glucos-3-O-yl-acetyl-L-alanyl-D-isoglutamine,
4,6-di-O-octanoyl-2-methoxyacetamido-2-deoxy-D-glucos-3-O-yl-acetyl-L-alanyl-D-isoglutamine,
4,6-di-O-octanoyl-2-myristamido-2-deoxy-D-glucos-3-O-yl-acetyl-L-alanyl-D-isoglutamine,
4,6-di-O-lauroyl-2-acetamido-2-deoxy-D-glucos-3-O-yl-acetyl-L-alanyl-D-isoglutamine,
4,6-di-O-lauroyl-2-acetamido-2-deoxy-D-glucos-3-O-yl-acetyl-L-valyl-D-isoglutamine,
4,6-di-O-lauroyl-2-acetamido-2-deoxy-D-glucos-3-O-yl-acetyl-L-prolyl-D-isoglutamine,
4,6-di-O-lauroyl-2-acetamido-2-deoxy-D-glucos-3-O-yl-acetyl-L-seryl-D-isoglutamine, 4,6-di-O-lauroyl-2-acetamido-2-deoxy-D-glucos-3-O-yl-acetyl-L-phenylalanyl-D-isoglutamine,
4,6-di-O-lauroyl-2-glycolamido-2-deoxy-D-glucos-3-O-yl-acetyl-L-alanyl-D-isoglutamine,
4,6-di-O-lauroyl-2-glycolamido-2-deoxy-D-glucos-3-O-yl-acetyl-L-valyl-D-isoglutamine,
4,6-di-O-lauroyl-2-glycolamido-2-deoxy-D-glucos-3-O-yl-acetyl-L-propyl-D-isoglutamine,
4,6-di-O-lauroyl-2-glycolamido-2-deoxy-D-glucos-3-O-yl-acetyl-L-seryl-D-isoglutamine,
4,6-di-O-lauroyl-2-glycolamido-2-deoxy-D-glucos-3-O-yl-acetyl-L-phenylalanyl-D-isoglutamine,
4,6-di-O-lauroyl-2-benzamido-2-deoxy-D-glucos-3-O-yl-acetyl-L-alanyl-D-isoglutamine,
4,6-di-O-lauroyl-2-trifluoroacetamido-2-deoxy-D-glucos-3-O-acetyl-L-alanyl-D-isoglutamine,
4,6-di-O-lauroyl-2-methoxyacetamido-2-deoxy-D-glucos-3-O-yl-acetyl-L-alanyl-D-isoglutamine,
4,6-di-O-lauroyl-2-myristamido-2-deoxy-D-glucos-3-O-yl-acetyl-L-alanyl-D-isoglutamine.
4,6-di-O-stearoyl-2-acetamido-2-2-deoxy-D-glucos-3-O-yl-acetyl-L-alanyl-D-isoglutamine,
4,6-di-O-stearoyl-2-acetamido-2-deoxy-D-glucos-3-O-yl-acetyl-L-valyl-D-isoglutamine,
4,6-di-O-stearoyl-2-acetamido-2-deoxy-D-glucos-3-O-yl-acetyl-L-prolyl-D-isoglutamine,
4,6-di-O-stearoyl-2-acetamido-2-deoxy-D-glucos-3-O-yl-acetyl-L-seryl-D-isoglutamine,
4,6-di-O-stearoyl-2-acetamido-2-deoxy-D-glucos-3-O-yl-acetyl-L-phenylalanyl-D-isoglutamine,
4,6-di-O-stearoyl-2-glycolamido-2-deoxy-D-glucos-3-O-yl-acetyl-L-alanyl-D-isoglutamine,
4,6-di-O-stearoyl-2-glycolamido-2-deoxy-D-glucos-3-O-yl-acetyl-L-valyl-D-isoglutamine,
4,6-di-O-stearoyl-2-glycolamido-2-deoxy-D-glucos-3-O-yl-acetyl-L-prolyl-D-isoglutamine,
4,6-di-O-stearoyl-2-glycolamido-2-deoxy-D-glucos-3-O-yl-acetyl-L-seryl-D-isoglutamine,
4,6-di-O-stearoyl-2-glycolamido-2-deoxy-D-glucos-3-O-yl-acetyl-L-phenylalanyl-D-isoglutamine,
4,6-di-O-stearoyl-2-benzamido-2-deoxy-D-glucos-3-O-yl-acetyl-L-alanyl-D-isoglutamine,
4,6-di-O-stearoyl-2-trifluoroacetamide-2-deoxy-D-glucos-3-O-yl-acetyl-L-alanyl-D-isoglutamine,
4,6-di-O-stearoyl-2-methoxyacetamido-2-deoxy-D-glucos-3-O-yl-acetyl-L-alanyl-D-isoglutamine, and
4,6-di-O-stearoyl-2-myristamido-2-deoxy-D-glucos-3-O-yl-acetyl-L-alanyl-D-isoglutamine.
4,6-di-O-benzoyl-2-acetamido-2-deoxy-D-glucos-3-O-yl-acetyl-L-alanyl-D-isoglutamine,
4,6-di-O-benzoyl-2-acetamido-2-deoxy-D-glucos-3-O-yl-acetyl-L-valyl-D-isoglutamine,
4,6-di-O-benzoyl-2-acetamido-2-deoxy-D-glucos-3-O-yl-acetyl-L-prolyl-D-isoglutamine,
4,6-di-O-benzoyl-2-acetamido-2-deoxy-D-glucos-3-O-yl-acetyl-L-seryl-D-isoglutamine,
4,6-di-O-benzoyl-2-acetamido-2-deoxy-D-glucos-3-O-yl-acetyl-L-phenylalanyl-D-isoglutamine,
4,6-di-O-benzoyl-2-glycolamido-2-deoxy-D-glucos-3-O-yl-acetyl-L-alanyl-D-isoglutamine,
4,6-di-O-benzoyl-2-glycolamido-2-deoxy-D-glucos-3-O-yl-acetyl-L-valyl-D-isoglutamine,
4,6-di-O-benzoyl-2-glycolamido-2-deoxy-D-glucos-3-O-yl-acetyl-L-prolyl-D-isoglutamine,
4,6-di-O-benzoyl-2-glycolamido-2-deoxy-D-glucos-3-O-yl-acetyl-L-seryl-D-isoglutamine,
4,6-di-O-benzoyl-2-glycolamido-2-deoxy-D-glucos-3-O-yl-acetyl-L-phenylalanyl-D-isoglutamine,
4,6-di-O-benzoyl-2-benzamido-2-deoxy-D-glucos-3-O-yl-acetyl-L-alanyl-D-isoglutamine,
4,6-di-O-benzoyl-2-trifluoroacetamido-2-deoxy-D-glucos-3-O-yl-acetyl-L-alanyl-D-isoglutamine,
4,6-di-O-benzoyl-2-methoxyacetamido-2-deoxy-D-glucos-3-O-yl-acetyl-L-alanyl-D-isoglutamine, and
4,6-di-O-benzoyl-2-myristamido-2-deoxy-D-glucos-3-3-O-yl-acetyl-L-alanyl-D-isoglutamine.

In like manner substituting a stoichiometric equivalent amount of the various products from Example 12 for benzyl (benzyl 2-acetamido-4,6-O-benzylidene-2-deoxy-α-D-glucopyranosid-3-O-yl) acetyl-L-alanyl-D-isoglutaminate there are obtained the corresponding compounds of Formula (13). Representative compounds thus obtained are:

4-O-acetyl-2-acetamido-2-deoxy-D-glucos-3-O-yl-acetyl-L-alanyl-D-isoglutamine,
4-O-acetyl-2-acetamido-2-deoxy-D-glucos-3-O-yl-acetyl-L-valyl-D-isoglutamine,
4-O-acetyl-2-acetamido-2-deoxy-D-glucos-3-O-yl-acetyl-L-prolyl-D-isoglutamine,
4-O-acetyl-2-acetamido-2-deoxy-D-glucos-3-O-yl-acetyl-L-seryl-D-isoglutamine,
4-O-acetyl-2-acetamido-2-deoxy-D-glucos-3-O-yl-acetyl-L-phenylalanyl-D-isoglutamine,
4-O-acetyl-2-glycolamido-2-deoxy-D-glucos-3-O-yl-acetyl-L-alanyl-D-isoglutamine,
4-O-acetyl-2-glycolamido-2-deoxy-D-glucos-3-O-yl-acetyl-L-valyl-D-isoglutamine,
4-O-acetyl-2-glycolamido-2-deoxy-D-glucos-3-O-yl-acetyl-L-prolyl-D-isoglutamine,
4-O-acetyl-2-glycolamido-2-deoxy-D-glucos-3-O-yl-acetyl-L-seryl-D-isoglutamine,
4-O-acetyl-2-glycolamido-2-deoxy-D-glucos-3-O-yl-acetyl-L-phenylalanyl-D-isoglutamine,
4-O-acetyl-2-benzamido-2-deoxy-D-glucos-3-O-yl-acetyl-L-alanyl-D-isoglutamine,
4-O-acetyl-2-trifluoroacetamido-2-deoxy-D-glucos-3-O-yl-acetyl-L-alanyl-D-isoglutamine,
4-O-acetyl-2-methoxyacetamido-2-deoxy-D-glucos-3-O-yl-acetyl-L-alanyl-D-isoglutamine,
4-O-acetyl-2-myristamido-2-deoxy-D-glucos-3-O-yl-acetyl-L-alanyl-D-isoglutamine,
4-O-butyryl-2-acetamido-2-deoxy-D-glucos-3-O-yl-acetyl-L-alanyl-D-isoglutamine,
4-O-butyryl-2-acetamido-2-deoxy-D-glucos-3O-yl-acetyl-L-valyl-D-isoglutamine,
4-O-butyryl-2-acetamido-2-deoxy-D-glucos-3-O-yl-acetyl-L-prolyl-D-isoglutamine,
4-O-butyryl-2-acetamido-2-deoxy-D-glucos-3-O-yl-acetyl-L-seryl-D-isoglutamine,
4-O-butyryl-2-acetamido-2-deoxy-D-glucos-3-O-yl-acetyl-L-phenylalanyl-D-isoglutamine,
4-O-butyryl-2-glycolamido-2-deoxy-D-glucos-3-O-yl-acetyl-L-alanyl-D-isoglutamine,
4-O-butyryl-2-glycolamido-2-deoxy-D-glucos-3-O-yl-acetyl-L-valyl-D-isoglutamine,
4-O-butyryl-2-glycolamido-2-deoxy-D-glucos-3-O-yl-acetyl-L-prolyl-D-isoglutamine,
4-O-butyryl-2-glycolamido-2-deoxy-D-glucos-3-O-yl-acetyl-L-seryl-D-isoglutamine,
4-O-butyryl-2-glycolamido-2-deoxy-D-glucos-3-O-yl-acetyl-L-phenylalanyl-D-isoglutamine,
4-O-butyryl-2-benzamido-2-deoxy-D-glucos-3-O-yl-acetyl-L-alanyl-D-isoglutamine, 4-O-butyryl-2-trifluoroacetamido-2-deoxy-D-glucos-3-O-yl-acetyl-L-alanyl-D-isoglutamine,
4-O-butyryl-2-methoxyacetamido-2-deoxy-D-glucos-3-O-yl-acetyl-L-alanyl-D-isoglutamine,
4-O-butyryl-2-myristamido-2-deoxy-D-glucos-3-O-yl-acetyl-L-alanyl-D-isoglutamine,
4-O-octanoyl-2-acetamido-2-deoxy-D-glucos-3-O-yl-acetyl-L-alanyl-D-isoglutamine,
4-O-octanoyl-2-acetamido-2-acetamido-2-deoxy-D-glucos-3-O-yl-acetyl-L-valyl-D-isoglutamine,
4-O-octanoyl-2-acetamido-2-deoxy-D-glucos-3-O-yl-acetyl-L-prolyl-D-isoglutamine,
4-O-octanoyl-2-acetamido-2-deoxy-D-glucos-3-O-yl-acetyl-L-seryl-D-isoglutamine,
4-O-octanoyl-2-acetamido-2-deoxy-D-glucos-3-O-yl-acetyl-L-phenylalanyl-D-isoglutamine,
4-O-octanoyl-2-glycolamido-2-deoxy-D-glucos-3-O-yl-acetyl-L-alanyl-D-isoglutamine,
4-O-octanoyl-2-glycolamido-2-deoxy-D-glucos-3-O-yl-acetyl-L-valyl-D-isoglutamine,
4-O-octanoyl-2-glycolamido-2-deoxy-D-glucos-3-O-yl-acetyl-L-prolyl-D-isoglutamine,
4-O-octanoyl-2-glycolamido-2-deoxy-D-glucos-3-O-yl-acetyl-L-seryl-D-isoglutamine,
4-O-octanoyl-2-glycolamido-2deoxy-D-glucos-3-O-yl-acetyl-L-phenylalanyl-D-isoglutamine,
4-O-octanoyl-2-benzamido-2-deoxy-D-glucos-3-O-yl-acetyl-L-alanyl-D-isoglutamine,
4-O-octanoyl-2-trifluoroacetamido-2-deoxy-D-glucos-3-O-yl-acetyl-L-alanyl-D-isoglutamine,
4-O-octanoyl-2-methoxyacetamido-2-deoxy-D-glucos-3-O-yl-acetyl-L-alanyl-D-isoglutamine,
4-O-octanoyl-2-myristamido-2-deoxy-D-glucos-3-O-yl-acetyl-L-alanyl-D-isoglutamine,
4-O-lauroyl-2-acetamido-2-deoxy-D-glucos-3-O-yl-acetyl-L-alanyl-D-isoglutamine,
4-O-lauroyl-2-acetamido-2-deoxy-D-glucos-3-O-yl-acetyl-L-valyl-D-isoglutamine,
4-O-lauroyl-2-acetamido-2-deoxy-D-glucos-3-O-yl-acetyl-L-prolyl-D-isoglutamine,
4-O-lauroyl-2-acetamido-2-deoxy-D-glucos-3-O-yl-acetyl-L-seryl-D-isoglutamine,
4-O-lauroyl-2-acetamido-2-deoxy-D-glucos-3-O-yl-acetyl-L-phenylalanyl-D-isoglutamine,
4-O-lauroyl-2-glycolamido-2-deoxy-D-glucos-3-O-yl-acetyl-L-alanyl-D-isoglutamine,
4-O-lauroyl-2-glycolamido-2-deoxy-D-glucos-3-O-yl-acetyl-L-valyl-D-isoglutamine,
4-O-lauroyl-2-glycolamido-2-deoxy-D-glucos-3-O-yl-acetyl-L-prolyl-D-isoglutamine,
4-O-lauroyl-2-glycolamido-2-deoxy-D-glucos-3-O-yl-acetyl-L-seryl-D-isoglutamine,
4-O-lauroyl-2-glycolamido-2-deoxy-D-glucos-3-O-yl-acetyl-L-phenylalanyl-D-isoglutamine,
4-O-lauroyl-2-benzamido-2-deoxy-D-glucos-3-O-yl-acetyl-L-alanyl-D-isoglutamine,
4-O-lauroyl-2-trifluoroacetamido-2-deoxy-D-glucos-3-O-yl-acetyl-L-alanyl-D-isoglutamine,
4-O-lauroyl-2-methoxyacetamido-2-deoxy-D-glucos-3-O-yl-acetyl-L-alanyl-D-isoglutamine,
4-O-lauroyl-2-myristamido-2-deoxy-D-glucos-3-O-yl-acetyl-L-alanyl-D-isoglutamine,
4-O-stearoyl-2-acetamido-2-deoxy-D-glucos-3-O-yl-acetyl-L-alanyl-D-isoglutamine,
4-O-stearoyl-2-acetamido-2-deoxy-D-glucos-3-O-yl-acetyl-L-valyl-D-isoglutamine,
4-O-stearoyl-2-acetamido-2-deoxy-D-glucos-3-O-yl-acetyl-L-prolyl-D-isoglutamine,
4-O-stearoyl-2-acetamido-2-deoxy-D-glucos-3-O-yl-acetyl-L-seryl-D-isoglutamine,
4-O-stearoyl-2-acetamido-2-deoxy-D-glucos-3-O-yl-acetyl-L-phenylalanyl-D-isoglutamine,
4-O-stearoyl-2-glycolamido-2-deoxy-D-glucos-3-O-yl-acetyl-L-alanyl-D-isoglutamine,
4-O-stearoyl-2-glycolamido-2-deoxy-D-glucos-3-O-yl-acetyl-L-valyl-D-isoglutamine,
4-O-stearoyl-2-glycolamido-2-deoxy-D-glucos-3-O-yl-acetyl-L-prolyl-D-isoglutamine,
4-O-stearoyl-2-glycolamido-2-deoxy-D-glucos-3-O-yl-acetyl-L-seryl-D-isoglutamine,
4-O-stearoyl-2-glycolamido-2-deoxy-D-glucos-3-O-yl-acetyl-L-phenylalanyl-D-isoglutamine,
4-O-stearoyl-2-benzamido-2-deoxy-D-glucos-3-O-yl-acetyl-L-alanyl-D-isoglutamine,
4-O-stearoyl-2-trifluoroacetamido-2-dexoy-D-glucos-3-O-yl-acetyl-L-alanyl-D-isoglutamine,
4-O-stearoyl-2-methoxyacetamido-2-deoxy-D-glucos-3-O-yl-acetyl-L-alanyl-D-isoglutamine,
4-O-stearoyl-2-myristamido-2-deoxy-D-glucos-3-O-yl-acetyl-L-alanyl-D-isoglutamine,
4-O-benzoyl-2-acetamido-2-deoxy-D-glucos-3-O-yl-acetyl-L-alanyl-D-isoglutamine,
4-O-benzoyl-2-acetamido-2-deoxy-D-glucos-3-O-yl-acetyl-L-valyl-D-isoglutamine,
4-O-benzoyl-2-acetamido-2-deoxy-D-glucos-3-O-yl-acetyl-L-prolyl-D-isoglutamine,
4-O-benzoyl-2-acetamido-2-deoxy-D-glucos-3-O-yl-acetyl-L-seryl-D-isoglutamine,
4-O-benzoyl-2-acetamido-2-deoxy-D-glucos-3-O-yl-acetyl-L-phenylalanyl-D-isoglutamine,
4-O-benzoyl-2-glycolamido-2-deoxy-D-glucos-3-O-yl-acetyl-L-alanyl-D-isoglutamine,
4-O-benzoyl-2-glycolamido-2-deoxy-D-glucos-3-O-yl-acetyl-L-valyl-D-isoglutamine,
4-O-benzoyl-2-glycolamido-2-deoxy-D-glucos-3-O-yl-acetyl-L-prolyl-D-isoglutamine,
4-O-benzoyl-2-glycolamido-2-deoxy-D-glucos-3-O-yl-acetyl-L-seryl-D-isoglutamine,
4-O-benzoyl-2-glycolamido-2-deoxy-D-glucos-3-O-yl-acetyl-L-phenylalanyl-D-isoglutamine,
4-O-benzoyl-2-benzamido-2-deoxy-D-glucos-3-O-yl-acetyl-L-alanyl-D-isoglutamine,
4-O-benzoyl-2-trifluoroacetamido-2-deoxy-D-glucos-3-O-yl-acetyl-L-alanyl-D-isoglutamine,
4-O-benzoyl-2-methoxyacetamido-2-deoxy-D-glucos-3-O-yl-acetyl-L-alanyl-D-isoglutamine, and
4-O-benzoyl-2-myristamido-2-deoxy-D-glucos-3-O-yl-acetyl-L-alanyl-D-isoglutamine.

In like manner substituting a stoichiometric equivalent amount of the various products from Example 13 for benzyl (benzyl 2-acetamido-4,6-O-benzylidene-2-deoxy-α-D-glucopyranosid-3-O-yl) acetyl-L-alanyl D-isoglutaminate there are obtained the corresponding compounds of Formula (13). Representative compounds thus obtained are:

4-O-acetyl-6-O-butyryl-2-acetamido-2-deoxy-D-glucos-3-O-yl-acetyl-L-alanyl-D-isoglutamine,
4-O-acetyl-6-O-butyryl-2-acetamido-2-deoxy-D-glucos-3-O-yl-acetyl-L-valyl-D-isoglutamine,
4-O-acetyl-6-O-butyryl-2-acetamido-2-deoxy-D-glucos-3-O-yl-acetyl-L-prolyl-D-isoglutamine,
4-O-acetyl-6-O-butyryl-2-acetamido-2-deoxy-D-glucos-3-O-yl-acetyl-L-seryl-D-isoglutamine, 4-O-acetyl-6-O-butyryl-2-acetamido-2-deoxy-D-glucos-3-O-yl-acetyl-L-phenylalanyl-D-isoglutamine,
4-O-acetyl-6-O-butyryl-2-glycolamido-2-deoxy-D-glucos-3-O-yl-acetyl-L-alanyl-D-isoglutamine,
4-O-acetyl-6-O-butyryl-2-glycolamido-2-deoxy-D-glucos-3-O-yl-acetyl-L-valyl-D-isoglutamine,
4-O-acetyl-6-O-butyryl-2-glycolamido-2-deoxy-D-glucos-3-O-yl-acetyl-L-prolyl-D-isoglutamine,
4-O-acetyl-6-O-butyryl-2-glycolamido-2-deoxy-D-glucos-3-O-yl-acetyl-L-seryl-D-isoglutamine,
4-O-acetyl-6-O-butyryl-2-glycolamido-2-deoxy-D-glucos-3-O-yl-acetyl-L-phenylalanyl-D-isoglutamine,
4-O-acetyl-6-O-butyryl-2-benzamido-2-deoxy-D-glucos-3-O-yl-acetyl-L-alanyl-D-isoglutamine,
4-O-acetyl-6-O-butyryl-2-trifluoroacetamido-2-deoxy-D-glucos-3-O-yl-acetyl-L-alanyl-D-isoglutamine,
4-O-acetyl-6-O-butyryl-2-methoxyacetamido-2-deoxy-D-glucos-3-O-yl-acetyl-L-alanyl-D-isoglutamine,
4-O-acetyl-6-O-butyryl-2-myristamido-2-deoxy-D-glucos-3-O-yl-acetyl-L-alanyl-D-isoglutamine,
4-O-acetyl-6-O-octanoyl-2-acetamido-2-deoxy-D-glucos-3-O-yl-acetyl-L-alanyl-D-isoglutamine,
4-O-acetyl-6-O-octanoyl-2-acetamido-2-deoxy-D-glucos-3-O-yl-acetyl-L-valyl-D-isoglutamine,
4-O-acetyl-6-O-octanoyl-2-acetamido-2-deoxy-D-glucos-3-O-yl-acetyl-L-prolyl-D-isoglutamine,
4-O-acetyl-6-O-octanoyl-2-acetamido-2-deoxy-D-glucos-3-O-yl-acetyl-L-seryl-D-isoglutamine,
4-O-acetyl-6-O-octanoyl-2-acetamido-2-deoxy-D-glucos-3-O-yl-acetyl-L-phenylalanyl-D-isoglutamine,
4-O-acetyl-6-O-octanoyl-2-glycolamido-2-dexoy-D-glucos-3-O-yl-acetyl-L-alanyl-D-isoglutamine,
4-O-acetyl-6-O-octanoyl-2-glycolamido-2-deoxy-D-glucos-3-O-yl-acetyl-L-valyl-D-isoglutamine,
4-O-acetyl-6-O-octanoyl-2-glycolamido-2-deoxy-D-glucos-3-O-yl-acetyl-L-prolyl-D-isoglutamine,
4-O-acetyl-6-O-octanoyl-2-glycolamido-2-deoxy-D-glucos-3-O-yl-acetyl-L-seryl-D-isoglutamine,
4-O-acetyl-6-O-octanoyl-2-glycolamido-2-deoxy-d-glucos-3-O-yl-acetyl-L-phenylalanyl-D-isoglutamine,
4-O-acetyl-6-O-octanoyl-2-benzamido-2-deoxy-D-glucos-3-O-yl-acetyl-L-alanyl-D-isoglutamine,
4-O-acetyl-6-O-octanoyl-2-trifluoroacetamido-2-deoxy-D-glucos-3-O-yl-acetyl-L-alanyl-D-isoglutamine,
4-O-acetyl-6-O-octanoyl-2-methoxyacetamido-2-deoxy-D-glucos-3-O-yl-acetyl-L-alanyl-D-isoglutamine,
4-O-acetyl-6-O-octanoyl-2-myristamido-2-deoxy-D-glucos-3-O-yl-acetyl-L-alanyl-D-isoglutamine,
4-O-acetyl-6-O-lauroyl-2-acetamido-2-deoxy-D-glucos-3-O-yl-acetyl-L-alanyl-D-isoglutamine,
4-O-acetyl-6-O-lauroyl-2-acetamido-2-deoxy-D-glucos-3-O-yl-acetyl-L-valyl-D-isoglutamine,
4-O-acetyl-6-O-lauroyl-2-acetamido-2-deoxy-D-glucos-3-O-yl-acetyl-L-prolyl-D-isoglutamine,
4-O-acetyl-6-O-lauroyl-2-acetamido-2-deoxy-D-glucos-3-O-yl-acetyl-L-seryl-D-isoglutamine,
4-O-acetyl-6-O-lauroyl-2-acetamdio-2-deoxy-D-glucos-3-O-yl-acetyl-L-phenylalanyl-D-isoglutamine,
4-O-acetyl-6-O-lauroyl-2-glycolamido-2-deoxy-D-glucos-3-O-yl-acetyl-L-alanyl-D-isoglutamine,
4-O-acetyl-6-O-lauroyl-2-glycolamido-2-deoxy-D-glucos-3-O-yl-acetyl-L-valvyl-D-isoglutamine,
4-O-acetyl-6-O-lauroyl-2-glycolamido-2-deoxy-D-glucos-3-O-yl-acetyl-L-prolyl-D-isoglutamine,
4-O-acetyl-6-O-lauroyl-2-glycolamido-2-deoxy-D-glucos-3-O-yl-acetyl-L-seryl-D-isoglutamine,
4-O-acetyl-6-O-lauroyl-2-glycolamido-2-deoxy-D-glucos-3-O-yl-acetyl-L-phenylalanyl-D-isoglutamine,
4-O-acetyl-6-O-lauroyl-2-benzamido-2-deoxy-D-glucos-3-O-yl-acetyl-L-alanyl-D-isoglutamine,
4-O-acetyl-6-O-lauroyl-2-trifluoroacetamido-2-deoxy-D-glucos-3-O-yl-acetyl-L-alanyl-D-isoglutamine,
4-O-acetyl-6-O-lauroyl-2-methoxyacetamido-2-deoxy-D-glucos-3-O-yl-acetyl-L-alanyl-D-isoglutamine,
4-O-acetyl-6-O-lauroyl-2-myristamido-2-deoxy-D-glucos-3-O-yl-acetyl-L-alanyl-D-isoglutamine,
4-O-acetyl-6-O-stearoyl-2-acetamido-2-deoxy-D-glucos-3-O-yl-acetyl-L-alanyl-D-isoglutamine,
4-O-acetyl-6-O-stearoyl-2-acetamido-2-deoxy-D-glucos-3-O-yl-acetyl-L-valyl-D-isoglutamine,
4-O-acetyl-6-O-stearoyl-2-acetamido-2-deoxy-D-glucos-3-O-yl-acetyl-L-prolyl-D-isoglutamine,
4-O-acetyl-6-O-stearoyl-2-acetamido-2-deoxy-D-glucos-3-O-yl-acetyl-L-seryl-D-isoglutamine,
4-O-acetyl-6-O-stearoyl-2-acetamido-2-deoxy-D-glucos-3-O-yl-acetyl-L-phenylalanyl-D-isoglutamine,
4-O-acetyl-6-O-stearoyl-2-glycolamido-2-deoxy-D-glucos-3-O-yl-acetyl-L-alanyl-D-isoglutamine,
4-O-acetyl-6-O-stearoyl-2-glycolamido-2-deoxy-D-glucose-3-O-yl-acetyl-L-valyl-D-isoglutamine,
4-O-acetyl-6-O-stearoyl-2-glycolamido-2-deoxy-D-gluco-3-O-yl-acetyl-L-prolyl-D-isoglutamine,
4-O-acetyl-6-O-stearoyl-2-glycolamido-2-deoxy-D-glucos-3-O-yl-acetyl-L-seryl-D-isoglutamine,
4-O-acetyl-6-O-stearoyl-2-glycolamido-2-deoxy-D-glucos-3-O-yl-acetyl-L-phenylalanyl-D-isoglutamine,
4-O-acetyl-6-O-stearoyl-2-benzamido-2-deoxy-D-glucos-3-O-yl-acetyl-L-alanyl-D-isoglutamine,
4-O-acetyl-6-O-stearoyl-2-trifluoroacetamido-2-deoxy-D-glucos-3-O-yl-acetyl-L-alanyl-D:isoglutamine,
4-O-acetyl-6-O-stearoyl-2-methoxyacetamido-2-deoxy-D-glucos-3-O-yl-acetyl-L-alanyl-D-isoglutamine, and
4-O-acetyl-6-O-stearoyl-2-myristamido-2-deoxy-D-glucos-3-O-yl-acetyl-L-alanyl-D-isoglutamine.
4-O-acetyl-6-O-benzoyl-2-acetamido-2-deoxy-D-glucos-3-O-yl-acetyl-L-alanyl-D-isoglutamine,
4-O-acetyl-6-O-benzoyl-2-acetamido-2-deoxy-D-glucos-3-O-yl-acetyl-L-valyl-D-isoglutamine,
4-O-acetyl-6-O-benzoyl-2-acetamido-2-deoxy-D-glucos-3-O-yl-acetyl-L-prolyl-D-isoglutamine,
4-O-acetyl-6-O-benzoyl-2-acetamido-2-deoxy-D-glucos-3-O-yl-acetyl-L-seryl-D-isoglutamine,
4-O-acetyl-6-O-benzoyl-2-acetamido-2-deoxy-D-glucos-3-O-yl-acetyl-L-phenylalanyl-D-isoglutamine,
4-O-acetyl-6-O-benzoyl-2-glycolamido-2-deoxy-D-glucos-3-O-yl-acetyl-L-alanyl-D-isoglutamine,
4-O-acetyl-6-O-benzoyl-2-glycolamido-2-deoxy-D-glucos-3-O-yl-acetyl-L-valyl-D-isoglutamine,
4-O-acetyl-6-O-benzoyl-2-glycolamido-2-deoxy-D-glucos-3-O-yl-acetyl-L-prolyl-D-isoglutamine,
4-O-acetyl-6-O-benzoyl-2-glycolamido-2-deoxy-D-glucos-3-O-yl-acetyl-L-seryl-D-isoglutamine,
4-O-acetyl-6-O-benzoyl-2-glycolamido-2-deoxy-D-glucos-3-O-yl-acetyl-L-phenylalanyl-D-isoglutamine,
4-O-acetyl-6-O-benzoyl-2-benzamido-2-deoxy-D-glucos-3-O-yl-acetyl-L-alanyl-D-sioglutamine, 4-O-acetyl-6-O-benzoyl-2-trifluroacetamido-2-deoxy-D-glucos-3-O-yl-acetyl-L-alanyl-D-isoglutamine,
4-O-acetyl-6-O-benzoyl-2-methoxyacetamido-2-deoxy-D-glucos-3-O-yl-acetyl-L-alanyl-D-isoglutamine,
4-O-acetyl-6-O-benzoyl-2-myristamido-2-deoxy-D-glucos-3-O-yl-acetyl-L-alanyl-D-isoglutamine,
4-O-butyryl-6-O-acetyl-2-acetamido-2-deoxy-D-glucos-3-O-yl-acetyl-L-alanyl-D-isoglutamine,
4-O-butyryl-6-O-acetyl-2-acetamido-2-deoxy-D-glucos-3-O-yl-acetyl-L-valyl-D-isoglutamine,
4-O-butyryl-6-O-acetyl-2-acetamido-2-deoxy-D-glucos-3-O-yl-acetyl-L-prolyl-D-isoglutamine,
4-O-butyryl-6-O-acetyl-2-acetamido-2-deoxy-D-glucos-3-O-yl-acetyl-L-seryl-D-isoglutamine,
4-O-butyryl-6-O-acetyl-2-acetamido-2-deoxy-D-glucos-3-O-yl-acetyl-L-phenylalanyl-D-isoglutamine,
4-O-butyryl-6-O-acetyl-2-glycolamido-2-deoxy-D-glucos-3-O-yl-acetyl-L-alanyl-D-isoglutamine,
4-O-butyryl-6-O-acetyl-2-glycolamido-2-deoxy-D-glucos-3-O-yl-acetyl-L-valyl-D-isoglutamine,
4-O-butyryl-6-O-acetyl-2-glycolamido-2-deoxy-D-glucos-3-O-yl-acetyl-L-prolyl-D-isoglutamine,
4-O-butyryl-6-O-acetyl-2-glycolamido-2-deoxy-D-glucos-3-O-yl-acetyl-L-seryl-D-isoglutamine,
4-O-butyryl-6-O-acetyl-2-glycolamido-2-deoxy-D-glucos-3-O-yl-acetyl-L-phenylalanyl-D-isoglutamine,
4-O-butyryl-6-O-acetyl-2-benzamido-2-deoxy-D-glucos-3-O-yl-acetyl-L-alanyl-D-isoglutamine,
4-O-butyryl-6-O-acetyl-2-trifluoroacetamido-2-deoxy-D-glucos-3-O-yl-acetyl-L-alanyl-D-isoglutamine,
4-O-butyryl-6-O-acetyl-2-methoxyacetamido-2-deoxy-D-glucos-3-O-yl-acetyl-L-alanyl-D-isoglutamine,
4-O-butyryl-6-O-acetyl-2-myristamido-2-deoxy-D-glucos-3-O-yl-acetyl-L-alanyl-D-isoglutamine,
4-O-octanoyl-6-O-acetyl-2-acetamido-2-deoxy-D-glucos-3-O-yl-acetyl-L-alanyl-D-isoglutamine,
4-O-octanoyl-6-O-acetyl-2-acetamido-2-deoxy-D-glucos-3-O-yl-acetyl-L-valyl-D-isoglutamine,
4-O-octanoyl-6-O-acetyl-2-acetamido-2-deoxy-D-glucos-3-O-yl-acetyl-L-prolyl-D-isoglutamine,
4-O-octanoyl-6-O-acetyl-2-acetamido-2-deoxy-D-glucos-3-O-yl-acetyl-L-seryl-D-isoglutamine,
4-O-octanoyl-6-O-acetyl-2-acetamido-2-deoxy-D-glucos-3-O-yl-acetyl-L-phenylalanyl-D-isoglutamine,
4-O-octanoyl-6-O-acetyl-2-glycolamido-2-deoxy-D-glucos-3-O-yl-acetyl-L-alanyl-D-isoglutamine,
4-O-octanoyl-6-O-acetyl-2-glycolamido-2-deoxy-D-glucos-3-O-yl-acetyl-L-valyl-D-isoglutamine,
4-O-octanoyl-6-O-acetyl-2-glycolamido-2-deoxy-D-glucos-3-O-yl-acetyl-L-prolyl-D-isoglutamine,
4-O-octanoyl-6-O-acetyl-2-glycolamido-2-deoxy-D-glucos-3-O-yl-acetyl-L-seryl-D-isoglutamine,
4-O-octanoly-6-O-acetyl-2-glycolamido-2-deoxy-D-glucos-3-O-yl-acetyl-L-phenylalanyl-D-isoglutamine,
4-O-octanoyl-6-O-acetyl-2-benzamido-2-deoxy-D-glucos-3-O-yl-acetyl-L-alanyl-D-isoglutamine,
4-O-octanoyl-6-O-acetyl-2-trifluoroacetamido-2-deoxy-D-glucos-3-O-yl-acetyl-L-alanyl-D-isoglutamine,
4-O-octanoyl-6-O-acetyl-2-methoxyacetamido-2-deoxy-D-glucos-3-O-yl-acetyl-L-alanyl-D-isoglutamine,
4-O-octanoyl-6-O-acetyl-2-myristamido-2-deoxy-D-glucos-3-O-yl-acetyl-L-alanyl-D-isoglutamine,
4-O-lauroyl-6-O-acetyl-2-acetamido-2-deoxy-D-glucos-3-O-yl-acetyl-L-alanyl-D-isoglutamine,
4-O-lauroyl-6-O-acetyl-2-acetamido-2-deoxy-D-glucos-3-O-yl-acetyl-L-valyl-D-isoglutamine,
4-O-lauroyl-6-O-acetyl-2-acetamido-2-deoxy-D-glucos-3-O-yl-acetyl-L-prolyl-D-isoglutamine,
4-O-lauroyl-6-O-acetyl-2-acetamido-2-deoxy-D-glucos-3-O-yl-acetyl-L-seryl-D-isoglutamine,
4-O-lauroyl-6-O-acetyl-2-acetamido-2-deoxy-D-glucos-3-O-acetyl-L-phenylalanyl-D-isoglutamine,
4-O-lauroyl-6-O-acetyl-2-glycolamido-2-deoxy-D-glucos-3-O-yl-acetyl-L-alanyl-D-isoglutamine,
4-O-lauroyl-6-O-acetyl-2-glycolamido-2-deoxy-D-glucos-3-O-yl-acetyl-L-valyl-D-isoglutamine,
4-O-lauroyl-6-O-acetyl-2-glycolamido-2-deoxy-D-glucos-3-O-yl-acetyl-L-prolyl-D-isoglutamine,
4-O-lauroyl-6-O-acetyl-2-glycolamido-2-deoxy-D-glucos-3-O-yl-acetyl-L-seryl-D-isoglutamine,
4-O-lauroyl-6-O-acetyl-2-glycolamido-2-deoxy-D-glucos-3-O-yl-acetyl-L-phenylalanyl-D-isoglutamine,
4-O-lauroyl-6-O-acetyl-2-benzamido-2-deoxy-D-glucos-3-O-yl-acetyl-L-alanyl-D-isoglutamine,
4-O-lauroyl-6-O-acetyl-2-trifluoroacetamido-2-deoxy-D-glucos-3-O-yl-acetyl-L-alanyl-D-isoglutamine,
4-O-lauroyl-6-O-acetyl-2-methoxyacetamido-2-deoxy-D-glucos-3-O-yl-acetyl-L-alanyl-D-isoglutamine, and
4-O-lauroyl-6-O-acetyl2-myristamido-2-deoxy-D-glucos-3-O-yl-acetyl-L-alanyl-D-isoglutamine.
4-O-stearoyl-6-O-acetyl-2-acetamido-2-deoxy-D-glucos-3-O-acetyl-L-alanyl-D-isoglutamine,
4-O-stearoyl-6-O-acetyl-2-acetamido-2-deoxy-D-glucos-3-O-yl-acetyl-L-valyl-D-isoglutamine,
4-O-stearoyl-6-O-acetyl-2-acetamido-2-acetamido-2-deoxy-D-glucos-3-O-yl-acetyl-L-prolyl-D-isoglutamine,
4-O-stearoyl-6-O-acetyl-2-acetamido-2-deoxy-D-glucos-3-O-yl-acetyl-L-seryl-D-isoglutamine,
4-O-stearoyl-6-O-acetyl-2-acetamido-2-deoxy-D-glucos-3-O-yl-acetyl-L-phenylalanyl-D-isoglutamine,
4-O-stearoyl-6-O-acetyl-2-glycolamido-2-deoxy-D-glucos-3-O-yl-acetyl-L-alanyl-D-isoglutamine,
4-O-stearoyl-6-O-acetyl-2-glycolamido-2-deoxy-D-glucos-3-O-yl-acetyl-L-valyl-D-isoglutamine,
4-O-stearoyl-6-O-acetyl-2-glycolamido-2-deoxy-D-glucos-3-O-yl-acetyl-L-prolyl-D-isoglutamine,
4-O-stearoyl-6-O-acetyl-2-glycolamido-2-deoxy-D-glucos-3-O-yl-acetyl-L-seryl-D-isoglutamine,
4-O-stearoyl-6-O-acetyl-2-glycolamido-2-deoxy-D-glucos-3-O-acetyl-L-phenylalanyl-D-isoglutamine,
4-O-stearoyl-6-O-acetyl-2-benzamido-2-deoxy-D-glucos-3-O-yl-acetyl-L-alanyl-D-isoglutamine,
4-O-stearoyl-6-O-acetyl-2-trifluoroacetamido-2-deoxy-D-glucos-3-O-yl-acetyl-L-alanyl-D-isoglutamine,
4-O-stearoyl-6-O-acetyl-2-methoxyacetamido-2-deoxy-D-glucos-3-O-yl-acetyl-L-alanyl-D-isoglutamine,
4-O-stearoyl-6-O-acetyl-2-myristamido-2-deoxy-D-glucos-3-O-yl-acetyl-L-alanyl-D-isoglutamine,
4-O-benzoyl-6-O-acetyl-2-acetamido-2-deoxy-D-glucos-3-O-yl-acetyl-L-alanyl-D-isoglutamine,
4-O-benzoyl-6-O-acetyl-2-acetamido-2-deoxy-D-glucos-3-O-yl-acetyl-L-valyl-D-isoglutamine,
4-O-benzoyl-6-O-acetyl-2-acetamido-2-deoxy-D-glucos-3-O-yl-acetyl-L-prolyl-D-isoglutamine,
4-O-benzoyl-6-O-acetyl-2-acetamido-2-deoxy-D-glucos-3-O-yl-acetyl-L-seryl-D-isoglutamine, 4-O-benzoyl-6-O-acetyl-2-acetamido-2-deoxy-D-glucos-3-O-yl-acetyl-L-phenylalanyl-D-isoglutamine,
4-O-benzoyl-6-O-acetyl-2-glycolamido-2-deoxy-D-glucos-3-O-yl-acetyl-L-alanyl-D-isoglutamine,
4-O-benzoyl-6-O-acetyl-2-glycolamido-2-deoxy-D-glucos-3-O-yl-acetyl-L-valyl-D-isoglutamine,
4-O-benzoyl-6-O-acetyl-2-glycolamido-2-deoxy-D-glucos-3-O-yl-acetyl-L-prolyl-D-isoglutamine,
4-O-benzoyl-6-O-acetyl-2-glycolamido-2-deoxy-D-glucos-3-O-yl-acetyl-L-seryl-D-isoglutamine,
4-O-benzoyl-6-O-acetyl-2-glycolamido-2-deoxy-D-glucos-3-O-yl-acetyl-L-phenylalanyl-D-isoglutamine,
4-O-benzoyl-6-O-acetyl-2-benzamido-2-deoxy-D-glucos-3-O-yl-acetyl-L-alanyl-D-isoglutamine,
4-O-benzoyl-6-O-acetyl-2-trifluoroacetamido-2-deoxy-D-glucos-3-O-yl-acetyl-L-alanyl-D-isoglutamine,
4-O-benzoyl-6-O-acetyl-2-methoxyacetamido-2-deoxy-D-glucos-3-O-yl-acetyl-L-alanyl-D-isoglutamine, and
4-O-benzoyl-6-O-acetyl-2-myristamido-2-deoxy-D-glucos-3-O-yl-acetyl-L-alanyl-D-isoglutamine.

In like manner substituting a stoichiometric equivalent amount of the various products from Example 14 for benzyl (benzyl 2-acetamido-4,6-O-benzylidene-2-deoxy-α-D-glucopyranosid-3-O-yl)acetyl-L-alanyl D-isoglutaminate there are obtained the corresponding compounds of Formula (13). Representative compounds thus obtaned are:

6-O-acetyl-2-acetamido-2-deoxy-D-glucos-3-O-yl-acetyl-L-alanyl-D-isoglutamine,
6-O-acetyl-2-acetamido-2-deoxy-D-glucos-3-O-yl-acetyl-L-valyl-D-isoglutamine,
6-O-acetyl-2-acetamido-2-deoxy-D-glucos-3-O-yl-acetyl-L-prolyl-D-isoglutamine,
6-O-acetyl-2-deoxy-D-glucos-3-O-acetyl-L-seryl-D-isoglutamine,
6-O-acetyl-2-acetamido-2-deoxy-D-glucos-3-O-yl-acetyl-L-phenylalanyl-D-isoglutamine,
6-O-acetyl-2-glycolamido-2-deoxy-D-glucos-3-O-yl-acetyl-L-alanyl-D-isoglutamine,
6-O-acetyl-2-glycolamido-2-deoxy-D-glucos-3-O-yl-acetyl-L-valyl-D-isoglutamine,
6-O-acetyl-2-glycolamido-2-deoxy-D-glucos-3-O-yl-acetyl-L-prolyl-D-isoglutamine,
6-O-acetyl-2-glycolamido-2-deoxy-D-glucos-3-O-yl-acetyl-L-seryl-D-isoglutamine,
6-O-acetyl-2-glycolamido-2-deoxy-D-glucos-3-O-yl-acetyl-L-phenylalanyl-D-isoglutamine,
6-O-acetyl-2-benzamido-2-deoxy-D-glucos-3-O-yl-acetyl-L-alanyl-D-isoglutamine,
6-O-acetyl-2-trifluoroacetamido-2-deoxy-D-glucos-3-O-yl-acetyl-L-alanyl-D-isoglutamine,
6-O-acetyl-2-methoxyacetamido-2-deoxy-D-glucos-3-O-yl-acetyl-L-alanyl-D-isoglutamine,
6-O-acetyl-2-myristamido-2-deoxy-D-glucos-3-O-yl-acetyl-L-alanyl-D-isoglutamine,
6-O-butyryl-2-acetamido-2-deoxy-D-glucos-3-O-yl-acetyl-L-alanyl-D-isoglutamine,
6-O-butyryl-2-acetamido-2-deoxy-D-glucos-3-O-yl-acetyl-L-valyl-D-isoglutamine,
6-O-butyryl-2-acetamido-2-deoxy-D-glucos-3-O-yl-acetyl-L-prolyl-D-isoglutamine,
6-O-butyryl-2-acetamido-2-deoxy-D-glucos-3-O-yl-acetyl-L-seryl-D-isoglutamine,
6-O-butyryl-2-acetamido-2-deoxy-D-glucos-3-O-yl-acetyl-L-phenylalanyl-D-isoglutamine,
6-O-butyryl-2-glycolamido-2-deoxy-D-glucos-3-O-yl-acetyl-L-alanyl-D-isoglutamine,
6-O-butyryl-2-glycolamido-2-deoxy-D-glucos-3-O-yl-acetyl-L-valyl-D-isoglutamine,
6-O-butyryl-2-glycolamido-2-deoxy-D-glucos-3-O-yl-acetyl-L-prolyl-D-isoglutamine,
6-O-butyryl-2-glycolamido-2-deoxy-D-glucos-3-O-yl-acetyl-L-seryl-D-isoglutamine,
6-O-butyryl-2-glycolamido-2-deoxy-D-glucos-3-O-yl-acetyl-L-phenylalanyl-D-isoglutamine,
6-O-butyryl-2-benzamido-2-deoxy-D-glucos-3-O-yl-acetyl-L-alanyl-D-isoglutamine,
6-O-butyryl-2-trifluoroacetamido-2-deoxy-D-glucos-3-O-yl-acetyl-L-alanyl-D-isoglutamine,
6-O-butyryl-2-methoxyacetamido-2-deoxy-D-glucos-3-O-yl-acetyl-L-alanyl-D-isoglutamine, and
6-O-butyryl-2-myristamido-2-deoxy-D-glucos-3-O-yl-acetyl-L-alanyl-D-isoglutamine.
6-O-octanoyl-2-acetamido-2-deoxy-D-glucos-3-O-yl-acetyl-L-alanyl-D-isoglutamine,
6-O-octanoyl-2-acetamido-2-deoxy-D-glucos-3-O-yl-acetyl-L-valyl-D-isoglutamine,
6-O-octanoyl-2-acetamido-2-deoxy-D-glucos-3-O-yl-acetyl-L-prolyl-D-isoglutamine,
6-O-octanoyl-2-acetamido-2-deoxy-D-glucos-3-O-yl-acetyl-L-seryl-D-isglutamine,
6-O-octanoyl-2-acetamido-2-deoxy-D-glucos-3-O-yl-acetyl-L-phenylalanyl-D-isoglutamine,
6-O-octanoyl-2-glycolamido-2-deoxy-D-glucos-3-O-yl-acetyl-L-alanyl-D-isoglutamine,
6-O-octanoyl-2-hglycolamido-2-deoxy-D-glucos-3-O-yl-acetyl-L-valyl-D-isoglutamine,
6-O-octanoyl-2-glycolamido-2-deoxy-D-glucos-3-O-yl-acetyl-L-prolyl-D-isoglutamine,
6-O-octanoyl-2-glycolamido-2-deoxy-D-glucos-3-O-yl-acetyl-L-seryl-D-isoglutamine,
6-O-octanoyl-2-glycolamido-2-deoxy-D-glucos-3-O-yl-acetyl-L-phenylalanyl-D-isoglutamine,
6-O-octanoyl-2-benzamido-2-deoxy-D-glucos-3-O-yl-acetyl-L-alanyl-D-isoglutamine,
6-O-octanoyl-2-trifluoroacetamido-2-deoxy-D-glucos-3-O-yl-acetyl-L-alanyl-D-isoglutamine,
6-O-octanoyl-2-methoxyacetamido-2-deoxy-D-glucos-3-O-yl-acetyl-L-alanyl-D-isoglutamine,
6-O-octanoyl-2-myristamido-2-deoxy-D-glucos-3-O-yl-acetyl-L-alanyl-D-isoglutamine,
6-O-lauroyl-2-acetamido-2-deoxy-D-glucos-3-O-yl-acetyl-L-alanyl-D-isoglutamine,
6-O-lauroyl-2-acetamido-2-deoxy-D-glucos-3-O-yl-acetyl-L-valyl-D-isoglutamine,
6-O-lauroyl-2-acetamido-2-deoxy-D-glucos-3-O-acetyl-L-prolyl-D-isoglutamine,
6-O-lauroyl-2-acetamido-2-deoxy-D-glucos-3-O-acetyl-L-seryl-D-isoglutamine,
6-O-lauroyl-2-acetamido-2-deoxy-D-glucos-3-O-yl-acetyl-L-phenylalanyl-D-isoglutamine,
6-O-lauroyl-2-glycolamido-2-deoxy-D-glucos-3-O-yl-acetyl-L-alanyl-D-isoglutamine,
6-O-lauroyl-2-glycolamido-2-deoxy-D-glucos-3-O-yl-acetyl-L-valyl-D-isoglutamine,
6-O-lauroyl-2-glycolamido-2-deoxy-D-glucos-3-O-yl-acetyl-L-prolyl-D-isoglutamine,
6-O-laruoyl-2-glycolamido-2-deoxy-D-glucos-3-O-yl-acetyl-L-seryl-D-isoglutamine,
6-O-lauroyl-2-glycolamido-2-deoxy-D-glucos-3-O-yl-acetyl-L-phenylalanyl-D-isoglutamine, 6-O-lauroyl-2-benzamido-2-deoxy-D-glucos-3-O-yl-acetyl-L-alanyl-D-isoglutamine,
6-O-lauroyl-2-trifluoroacetamido-2-deoxy-D-glucos-3-O-yl-acetyl-L-alanyl-D-isoglutamine,
6-O-lauroyl-2-methoxyacetamido-2-deoxy-D-glucos-3-O-yl-acetyl-L-alanyl-D-isoglutamine,
6-O-lauroyl-2-myristamido-2-deoxy-D-glucos-3-O-yl-acetyl-L-alanyl-D-isoglutamine,
6-O-stearoyl-2-acetamido-2-deoxy-D-glucos-3-O-yl-acetyl-L-alanyl-D-isoglutamine,
6-O-stearoyl-2-acetamido-2-deoxy-D-glucos-3-O-yl-acetyl-L-valyl-D-isoglutamine,
6-O-stearoyl-2-acetamido-2-deoxy-D-glucos-3-O-yl-acetyl-L-prolyl-D-isoglutamine,
6-O-stearoyl-2-acetamido-2-deoxy-D-glucos-3-O-yl-acetyl-seryl-D-isoglutamine,
6-O-stearoyl-2-acetamido-2-deoxy-D-glucos-3-O-yl-acetyl-L-phenylalanyl-D-isoglutamine,
6-O-stearoyl-2-glycolamido-2-deoxy-D-glucos-3-O-yl-acetyl-L-alanyl-D-isoglutamine,
A6-O-stearoyl-2-glycolamido-2-deoxy-D-glycos-3-O-yl-acetyl-L-valyl-D-isoglutamine,
6-O-stearoyl-2-glycolamido-2-deoxy-D-glucos-3-O-yl-acetyl-L-prolyl-D-isoglutamine,
6-O-stearoyl-2-glycolamido-2-deoxy-D-glucos-3-O-yl-acetyl-L-seryl-D-isoglutamine,
6-O-stearoyl-2-glycolamido-2-deoxy-D-glucos-3-O-yl-acetyl-L-phenylalanyl-D-isoglutamine,
6-O-stearoyl-2-benzamido-2-deoxy-D-glucos-3-O-yl-acetyl-L-alanyl-D-isoglutamine,
6-O-stearoyl-2-trifluoroacetamido-2-deoxy-D-glucos-3-O-acetyl-L-alanyl-D-isoglutamine,
6-O-stearoyl-2-methoxyacetamido-2-deoxy-D-glucos-3-O-yl-acetyl-L-alanyl-D-isoglutamine,
6-O-stearoyl-2-myristamido-2-dexoy-D-glucos-3-O-yl-acetyl-L-alanyl-D-isoglutamine,
6-O-benzoyl-2-acetamido-2-deoxy-D-glucos-3-O-yl-acetyl-L-alanyl-D-isoglutamine,
6-O-benzoyl-2-acetamido-2-deoxy-D-glucos-3-O-yl-acetyl-L-valyl-D-isoglutamine,
6-O-benzoyl-2-acetamido-2-deoxy-D-glucos-3-O-yl-acetyl-L-prolyl-D-isoglutamine,
6-O-benzoyl-2-acetamido-2-deoxy-D-glucos-3-O-yl-acetyl-L-seryl-D-isoglutamine,
6-O-benzoyl-2-acetamido-2-deoxy-D-glucos-3-O-yl-acetyl-L-phenylalanyl-D-isoglutamine,
6-O-benzoyl-2-glycolamido-2-deoxy-D-glucos-3-O-yl-acetyl-L-alanyl-D-isoglutamine,
6-O-benzoyl-2-glycolamido-2-deoxy-D-glucos-3-O-yl-acetyl-L-valyl-D-isoglutamine,
6-O-benzoyl-2-glycolamido-2-deoxy-D-glucos-3-O-yl-acetyl-prolyl-D-isoglutamine,
6-O-benzoyl-2-glycolamido-2-deoxy-D-glucos-3-O-yl-acetyl-L-seryl-D-isoglutamine,
6-O-benzoyl-2-glycolamido-2-deoxy-D-glucos-3-O-yl-acetyl-L-phenylalanyl-D-isoglutamine,
6-O-benzoyl-2-benzamido-2-deoxy-D-glucos-3-O-yl-acetyl-L-alanyl-D-isoglutamine,
6-O-benzoyl-2-trifluoroacetamido-2-deoxy-D-glucos-3-O-yl-acetyl-L-alanyl-D-isoglutamine,
6-O-benzoyl-2-methoxyacetamido-2-deoxy-D-glucos-3-O-yl-acetyl-L-alanyl-D-isoglutamine, and
6-O-benzoyl-2-myristamido-2-deoxy-D-glucos-3-O-yl-acetyl-L-alanyl-D-isoglutamine.

By the use of techniques well known to those skilled in the art of carbohydrate chemistry, and in particular by crystallization, the compounds of Formula (13) [and-/or Formula (I)] are separated into the individual α— and β— anomers.

EXAMPLE 16

The antigen mixture used consists of 20 μg. of arsanilic tyrosine and 100 μg. of protein [either bovine serum albumin (BSA) or ovalbumin]. The antigen mixture and the compounds to be tested, at the dose levels per guinea pig shown in the Table below, are dissolved in saline and emulsified with an equal volume of Freund's Incomplete Adjuvant (FIA). Groups of ten guinea pigs are used for each test compound and each guinea pig is injected with 0.1 ml. of the above emulsion, subcutaneously, in the nuchal region. Control groups are given the antigen mixture alone emulsified with FIA.

After 14 days, all animals are skin tested using 25 μg arsanilic tyrosine conjugated to either BSA or ovalbumin (BSA is used in this test when ovalbumin is present in the antigen mixture and vice versa) which is given in 0.1 ml saline intradermally in the flanks of the animals. The potencies of the test compounds in stimulating the delayed hypersensitivity reaction are then computed by multiplying the average area of the skin reaction at 24 hours by a number from 1 to 3 which is a measure of the amount of infiltration observed in each skin reaction. Thus, the procedure is as follows: skin tests with a high degree of infiltration are scored as + + and assigned the number 3; those with a lesser degree are scored as + and given the number 2, whereas skin reactions with no infiltration are scored as zero and assigned the number 1. These numbers are then totaled for the animals in a group and the average number obtained is then multiplied by the average area of the observed skin reaction. There is thus included in the potencies the amount of infiltration coupled with the average area observed in the skin test. Average potencies of the test compounds are presented in Column 1 in the Table below relative to FIA having the value of one.

On day 42 all animals are bled by cardiac puncture and the sera assayed for antibovine serum albumin or antiovalbumin antibodies by the passive hemagglutination technique or by radiommune assay using the Farr techbique (P. Minden and R.S. Farr in "Handbook of Experimental Immunology", edited by D.M. Weir, Chapter 15, Volume 1, Blackwell Scientific Publications, Oxford) using 125 iodine labeled bovine serum albumin. Average potencies of these assays are presented in Column 2 of the Table below relative to FIA having the value of one.

TABLE

| | | Average Potency | |
|---|---|---|---|
| Compound | Dose μg. | Column 1 Delayed Hypersensitivity to Arsanilic Tyrosine | Column 2 Antibody Titre |
| FIA | — | 1 | 1 |
| 2-(2-acetamido-2-deoxy-D-glucos-3-0-yl)-D-propionyl-L-alanyl-D-isoglutamine | 50 | 3.3 | 3.7 |
| 2-acetamido-2-deoxy-D-glucos-3-0-yl-acetyl-L-alanyl-D-isoglutamine | 50 | 5.7 | 5.1 |
| 2-acetamido-2-deoxy-D-glucos-3-0-yl-acetyl-L-seryl-D-isoglutamine | 50 | 14.7 | 19.7 |
| 2-acetamido-2-deoxy-d-glucos-3-0-yl-acetyl-L.-valyl-D-isoglutamine | 50 | 6.5 | 10.6 |
| 2-acetamido-2-deoxy-D-glucos-3-0-yl-acetyl-L-leucyl-D-isoglutamine | 50 | 0.9 | 1.6 |

TABLE-continued

| Compound | Dose μg. | Average Potency Column 1 Delayed Hypersensitivity to Arsanilic Tyrosine | Column 2 Antibody Titre |
|---|---|---|---|
| 2-acetamido-2-deoxy-D-glucos-3-0-yl-acetyl-L-lysyl-D-isoglutamane | 20 | 1.1 | 1.7 |
| 2-acetamido-2-deoxy-D-glucos-3-0-yl-acetyl-L-phenylalanyl-D-isoglutamine | 50 | 1.2 | 4.9 |
| 2-acetamido-2-deoxy-D-glucos-3-0-yl-acetyl-L-prolyl-D-isoglutamine | 50 | 5.4 | 8.0 |
| 2-acetamido-2-deoxy-D-glucos-3-0-yl-acetyl-L-tyrosyl-D-isoglutamine | 20 | 1.5 | 1.6 |
| 2-acetamido-2-deoxy-D-glucos-3-0-yl-acetyl-L-alanyl-D-isoasparagine | 50 | 1.5 | 2.1 |

EXAMPLE 17

A. 48 Dogs were divided into groups and inoculated with the amounts of compound (per kilogram of body weight) as shown in the following Table:

Table

| Group No. | No. of Dogs | 2-acetamido-2-deoxy-D-glucos-3-0-yl-D-lactyl-L-alanyl-D-isoglutamine | 2-acetamido-2-deoxy D-glucos-3-0-yl-acetyl-L-alanyl-D-isoglutamine |
|---|---|---|---|
| 1 | 4 | 1500 μg. | Nil |
| 2 | 4 | 600 μg. | Nil |
| 3 | 4 | 240 μg. | Nil |
| 4 | 4 | 96 μg. | Nil |
| 5 | 4 | 38.4 μg. | Nil |
| 6 | 4 | Nil | 1500 μg. |
| 7 | 4 | Nil | 600 μg. |
| 8 | 4 | Nil | 240 μg. |
| 9 | 4 | Nil | 96 μg. |
| 10 | 4 | Nil | 38.4 μg. |
| 11 | 8 | Nil | Nil |

The results were as follows:

(a) All of the dogs in Groups 1 and 2 and two of the dogs in Group 3 showed severe depression, excessive salivation and vomiting.

(b) None of the dogs in Groups 6 through 11 showed the severe symptoms described in (a) above. However, all of the dogs in Group 6, one dog in Group 7 and one dog in Group 11 (the controls) did show fasciculation (twitching) of the eye muscles, which may have been an aberrant symptom since all of the dogs having this symptom were from the same litter (and caged together during the test).

B. Seven cats were divided into groups and inoculated with the amounts of compounds (per kilogram of body weight) as shown in the following Table:

TABLE

| Group No. | No. of Cats | 2-acetamido-2-deoxy D-glucos-3-0-yl-D-lactyl-L-alanyl-D-isoglutamine | 2-acetamido-2-deoxy D-glucos-3-0-yl-acetyl-L-alanyl-D-isoglutamine |
|---|---|---|---|
| 1 | 3 | 1500 μg. | Nil |
| 2 | 3 | Nil | 1500 μg. |
| 3 | 1 | Nil | Nil |

The results were as follows:

(a) All of the cats in Group 1 vomited 4–6 times over a period of 2–5 hours post-inoculation. Initial vomitus was a dark fluid and later it became a clear froth after the stomach had emptied. All animals had diarrhea during the same period. Following the initial vomiting and diarrhea, animals became depressed and unkempt. Chin, neck, and forepaws became matted with saliva and vomitus remained hanging from their mouths. Food was refused when offered. Rectal temperatures elevated to a peak of 104° F seven hours post-inoculation. At 24 hours post-inoculation all animals had returned to normal.

(b) All of the cats in Group 2 remained normal following inoculation. They continued to play, climb the walls of the cage, wrestle, eat normally, and all physiological functions remained normal.

(c) The cat in Group 3 (the control) remained normal throughout the test.

What is claimed is:

1. A compound selected from those of the formula:

$$\text{(I)}$$

wherein
each of R and $R^1$ are the same or different and are selected from the group consisting of hydrogen or an acyl radical containing from 1 to 22 carbon atoms;
$R^2$ is selected from the group consisting of an unsubstituted or substituted alkyl radical containing from 1 to 22 carbon atoms, or an unsubstituted or substituted aryl radical containing from 6 to 10 carbon atoms;
X is an aminoacyl moiety selected from the group consisting of
L-alanyl,
L-valyl,
L-leucyl,
L-isoleucyl,
L-α-aminobutyryl,
L-seryl,
L-threonyl,
L-methionyl,
L-cysteinyl,
L-phenylalanyl,
L-tyrosyl,
L-tryptophanyl,
L-lysyl,
L-ornithyl,
L-arginyl,
L-histidyl,
L-glutamyl,
L-glutaminyl,
L-aspartyl,
L-asparaginyl,
L-prolyl, or
L-hydroxyprolyl;
Y is an amino acid moiety selected from the group consisting of D-isoasparagine and D-isoglutamine; and
the wavy lines (ξ) represent the α- or β-configuration or mixtures thereof, with the proviso that when one wavy line is α, the other is β.

2. A compound according to claim 1 wherein each of R and $R^1$ are hydrogen.

3. A compound according to claim 1 wherein $R^2$ is an unsubstituted alkyl radical containing from 1 to 22 carbon atoms.

4. A compound according to claim 1, wherein X is selected from the group consisting of L-alanyl, L-seryl, L-valyl or L-prolyl.

5. A compound according to claim 1, wherein Y is D-isoglutamine.

6. A compound according to claim 1, wherein R and $R^1$ are the same acyl radical containing from 1 to 22 carbon atoms.

7. A compound according to claim 1 wherein R is hydrogen and $R^1$ is an acyl radical containing from 1 to 22 carbon atoms.

8. A compound according to claim 1 wherein R is an acyl radical containing from 1 to 22 carbon atoms and $R^1$ is hydrogen.

9. A compound according to claim 1 wherein R and $R^1$ are different acyl radicals containing from 1 to 22 carbon atoms.

10. A compound according to claim 1 wherein $R^2$ is methyl.

11. A compound according to claim 1 wherein $R^2$ is hydroxymethyl.

12. A compound according to claim 1 wherein R and $R^1$ are both hydrogen, $R^2$ is methyl, Y is D-isoglutamine and X is selected from the group consisting of L-alanyl, L-seryl, L-valyl or L-prolyl.

13. A compound according to claim 1 wherein R and $R^1$ are both acetyl, $R^2$ is methyl, Y is D-isoglutamine and X is selected from the group consisting of L-alanyl, L-seryl, L-valyl or L-prolyl.

14. A compound according to claim 1 wherein R and $R^1$ are both butyryl, $R^2$ is methyl, Y is D-isoglutamine and X is selected from the group consisting of L-alanyl, L-seryl, L-valyl or L-prolyl.

15. A compound according to claim 1 wherein R and $R^1$ are both octanoyl, $R^2$ is methyl, Y is D-isoglutamine and X is selected from the group consisting of L-alanyl, L-seryl, L-valyl or L-prolyl.

16. A compound according to claim 1 wherein R and $R^1$ are both lauroyl, $R^2$ is methyl, Y is D-isoglutamine and X is selected from the group consisting of L-alanyl, L-seryl, L-valyl or L-prolyl.

17. A compound according to claim 1 wherein R and $R^1$ are both stearoyl, $R^2$ is methyl, Y is D-isoglutamine and X is selected from the group consisting of L-alanyl, L-seryl, L-valyl or L-prolyl.

18. A compound according to claim 1 wherein R is acetyl, $R^1$ is hydrogen, $R^2$ is methyl, Y is D-isoglutamine and X is selected from the group consisting of L-alanyl, L-seryl, L-valyl or L-prolyl.

19. A compound according to claim 1 wherein R is butyryl, $R^1$ is hydrogen, $R^2$ is methyl, Y is D-isoglutamine and X is selected from the group consisting of L-alanyl, L-seryl, L-valyl or L-prolyl.

20. A compound according to claim 1 wherein R is octanoyl, $R^1$ is hydrogen, $R^2$ is methyl, Y is D-isoglutamine and X is selected from the group consisting of L-alanyl, L-seryl, L-valyl or L-prolyl.

21. A compound according to claim 1 wherein R is lauroyl, $R^1$ is hydrogen, $R^2$ is methyl, Y is D-isoglutamine and X is selected from the group consisting of L-alanyl, L-seryl, L-valyl or L-prolyl.

22. A compound according to claim 1 wherein R is stearoyl, $R^1$ is hydrogen, $R^2$ is methyl, Y is D-isoglutamine and X is selected from the group consisting of L-alanyl, L-seryl, L-valyl or L-prolyl.

23. A compound according to claim 1 wherein $R^1$ is acetyl, R is hydrogen, $R^2$ is methyl, Y is D-isoglutamine and X is selected from the group consisting of L-alanyl, L-seryl, L-valyl or L-prolyl.

24. A compound according to claim 1 wherein $R^1$ is butyryl, R is hydrogen, $R^2$ is methyl, Y is D-isoglutamine and X is selected from the group consisting of L-alanyl, L-seryl, L-valyl or L-prolyl.

25. A compound according to claim 1 wherein $R^1$ is octanoyl, R is hydrogen, $R^2$ is methyl, Y is D-isoglutamine and X is selected from the group consisting of L-alanyl, L-seryl, L-valyl or L-prolyl.

26. A compound according to claim 1 wherein $R^1$ is lauroyl, R is hydrogen, $R^2$ is methyl, Y is D-isoglutamine and X is selected from the group consisting of L-alanyl, L-seryl, L-valyl or L-propyl.

27. A compound according to claim 1 wherein $R^1$ is stearoyl, R is hydrogen, $R^2$ is methyl, Y is D-isoglutamine and X is selected from the group consisting of L-alanyl, L-seryl, L-valyl or L-propyl.

28. A compound according to claim 1 wherein R is butyryl, $R^1$ is acetyl, $R^2$ is methyl, Y is D-isoglutamine and X is selected from the group consisting of L-alanyl, L-seryl, L-valyl or L-prolyl.

29. A compound according to claim 1 wherein R is octanoyl, $R^1$ is acetyl, $R^2$ is methyl, Y is D-isoglutamine and X is selected from the group consisting of L-alanyl, L-seryl, L-valyl or L-prolyl.

30. A compound according to claim 1 wherein R is lauroyl, $R^1$ is acetyl, $R^2$ is methyl, Y is D-isoglutamine and X is selected from the group consisting of L-alanyl, L-seryl, L-valyl or L-prolyl.

31. A compound according to claim 1 wherein $R^2$ is trifluoromethyl, R and $R^1$ are both hydrogen, Y is D-isoglutamine and X is selected from the group consisting of L-alanyl, L-seryl, L-valyl or L-prolyl.

32. A compound according to claim 1 wherein $R^2$ is n-undecyl, R and $R^1$ are both hydrogen, Y is D-isoglutamine and X is selected from the group consisting of L-alanyl, L-seryl, L-valyl or L-prolyl.

33. The compound according to claim 1 wherein R and $R^1$ are both hydrogen, $R^2$ is methyl, Y is D-isoglutamine and X is L-alanyl; 2-acetamido-2-deoxy-D-glucos-3-O-acetyl-L-alanyl-D-isoglutamine.

34. The compound according to claim 1 wherein R and $R^1$ are both hydrogen, $R^2$ is methyl, Y is D-isoglutamine and X is L-seryl; 2-acetamido-2-deoxy-D-glucos-3-O-yl-acetyl-L-seryl-D-isoglutamine.

35. The compound according to claim 1 wherein R and $R^1$ are both hydrogen, $R^2$ is methyl, Y is D-isoglutamine and X is L-valyl; 2-acetamido-2-deoxy-D-glucos-3-O-yl-acetyl-L-valyl-D-isoglutamine.

36. The compound according to claim 1 wherein R and $R^1$ are both hydrogen, $R^2$ is methyl, Y is D-isoglutamine and X is L-prolyl; 2-acetamido-2-deoxy-D-glucos-3-O-yl-acetyl-L-prolyl-D-isoglutamine.

37. The compound according to claim 1 wherein R and $R^1$ are both acetyl, $R^2$ is methyl, Y is D-isoglutamine and X is L-alanyl, 4,6-di-O-acetyl-2-acetamido-2-deoxy-D-glucos-3-O-yl-acetyl-L-alanyl-D-isoglutamine.

38. The compound according to claim 1 wherein R and $R^1$ are both butyryl, $R^2$ is methyl, Y is D-isoglutamine and X is L-alanyl; 4,6-di-O-butyryl-2-acetamido-2-deoxy-D-glucos-3-O-yl-acetyl-L-alanyl-D-isoglutamine.

39. The compound according to claim 1 wherein R and $R^1$ are both lauroyl, $R^2$ is methyl, Y is D-isoglutamine and X is L-alanyl; 4,6-di-O-lauroyl-2-acetamido-2- deoxy-D-glucos-3-O-yl-acetyl-L-alanyl-D-isoglutamine.

40. The compound according to claim 1 wherein R and R$^1$ are both acetyl, R$^2$ is methyl, Y is D-isoglutamine and X is L-prolyl; 4,6-di-O-acetyl-2-acetamido-2-deoxy-D-glucos-3-O-acetyl-L-prolyl-D-isoglutamine.

41. The compound according to claim 1 wherein R and R$^1$ are both butyryl, R$^2$ is methyl, Y is D-isoglutamine and X is L-prolyl; 4,6-di-O-butyryl-2-acetamido-2-deoxy-D-glucos-3-O-yl-acetyl-L-prolyl-D-isoglutamine.

42. The compound according to claim 1 wherein R and R$^1$ are both lauroyl, R$^2$ is methyl, Y is D-isoglutamine and X is L-prolyl; 4,6-di-O-lauroyl-2-acetamido-2-deoxy-D-glucos-3-O-yl-acetyl-L-prolyl-D-isoglutamine.

43. The compound according to claim 1 wherein R and R$^1$ are both hydrogen, R$^2$ is hydroxymethyl, Y is D-isoglutamine and X is L-alanyl; 2-glycolamido-2-deoxy-D-glucos-3-O-yl-acetyl-L-alanyl-D-isoglutamine.

44. The compound according to claim 1 wherein R and R$^1$ are both hydrogen, R$^2$ is hydroxymethyl, Y is D-isoglutamine and X is L-seryl; 2-glycolamido-2deoxy-D-glucose-3-O-yl-seryl-D-isoglutamine.

45. The compound according to claim 1 wherein R and R$^1$ are both hydrogen, R$^2$ is hydroxymethyl, Y is D-isoglutamine and X is L-valyl; 2-glycolamido-2-deoxy-D-glucos-3-O-yl-acetyl-L-valyl-D-isoglutamine.

46. The compound according to claim 1 wherein R and R$^1$ are both hydrogen, R$^2$ is hydroxymethyl, Y is D-isoglutamine and X is L-prolyl; 2-glycolamido-2-deoxy-D-glucos-3-O-yl-acetyl-L-prolyl-D-isoglutamine.

47. The compound according to claim 1 wherein R and R$^1$ are both acetyl, R$^2$ is hydroxymethyl, Y is D-isoglutamine and X is L-alanyl; 4,6-di-O-acetyl-2-glycolamido-2-deoxy-D-glucos-3-O-yl-acetyl-L-alanyl-D-isoglutamine.

48. The compound according to claim 1 wherein R and R$^1$ are both acetyl, R$^2$ is hydroxymethyl, Y is D-isoglutamine and X is L-seryl; 4,6-di-O-acetyl-2-deoxy-D-glucos-3-O-yl-acetyl-L-seryl-D-isoglutamine.

49. The compound according to claim 1 wherein R and R$^1$ are both acetyl, R$^2$ is hydroxymethyl, Y is D-isoglutamine and X is L-valyl; 4,6-di-O-acetyl-2-glycolamido-2-deoxy-D-glucos-3-O-yl-acetyl-L-valyl-D-isoglutamine.

50. The compound according to claim 1 wherein R and R$^1$ are both acetyl, R$^2$ is hydroxymethyl, Y is D-isoglutamine and X is L-prolyl; 4,6di-O-acetyl-2-glycolamido-2-deoxy-D-glucos-3-O-yl-acetyl-L-prolyl-D-isoglutamine.

* * * * *